(12) United States Patent
Gardner et al.

(10) Patent No.: US 12,076,521 B2
(45) Date of Patent: Sep. 3, 2024

(54) ANTISEPTIC CAP

(71) Applicant: Excelsior Medical Corporation, San Clemente, CA (US)

(72) Inventors: Christopher E. Gardner, Manalapan, NJ (US); William Anderson, Cary, IL (US); Bruce Nanyung Lin, Somerset, NJ (US)

(73) Assignee: Excelsior Medical Corporation, San Clemente, CA (US)

( * ) Notice: Subject to any disclaimer, the term of this patent is extended or adjusted under 35 U.S.C. 154(b) by 569 days.

(21) Appl. No.: 17/025,201

(22) Filed: Sep. 18, 2020

(65) Prior Publication Data

US 2021/0162194 A1 Jun. 3, 2021

Related U.S. Application Data

(63) Continuation of application No. 16/162,106, filed on Oct. 16, 2018, now Pat. No. 10,806,919, which is a
(Continued)

(51) Int. Cl.
*A61M 39/16* (2006.01)
*A61M 39/20* (2006.01)

(52) U.S. Cl.
CPC .......... *A61M 39/162* (2013.01); *A61M 39/20* (2013.01); *A61M 39/165* (2013.01); *A61M 2205/0205* (2013.01)

(58) Field of Classification Search
CPC ........ A61M 2205/0205; A61M 39/162; A61M 39/165; A61M 39/20
See application file for complete search history.

(56) References Cited

U.S. PATENT DOCUMENTS

| 382,297 A | 5/1888 | Fry |
| 559,697 A | 5/1896 | Tiugti et al. |

(Continued)

FOREIGN PATENT DOCUMENTS

| CA | 2 148 847 | 12/1995 |
| CA | 2 169 689 | 8/1996 |

(Continued)

OTHER PUBLICATIONS

"Small-bore connectors for liquids and gases in healthcare applications—Part : Connectors for intravascular or hypodermic applications," ISO 80369-7, Corrected version dated Dec. 1, 2016 (50 pages).
(Continued)

*Primary Examiner* — Brandy S Lee
(74) *Attorney, Agent, or Firm* — Knobbe, Martens, Olson and Bear, LLP

(57) ABSTRACT

An antiseptic dead-end cap includes a base having first and second sides, a first annular wall extending from the first side of the base, a cylindrical center plug extending from the first side of the base, and a second annular wall extending from the second side of the base. The first annular wall has an outer and an inner surface. The cylindrical center plug has an outer and an inner surface, and is positioned within the first annular wall to form an annular chamber. The second annular wall has an outer and an inner surface, and defines a second chamber having an open end. The second chamber is further defined by the inner surface of the cylindrical center plug. An antiseptic material is on at least one of the first annular wall inner surface, second annular wall inner surface, second annular wall outer surface, and cylindrical center plug outer surface.

8 Claims, 18 Drawing Sheets

Related U.S. Application Data continuation of application No. 13/803,289, filed on Mar. 14, 2013, now Pat. No. 10,166,381, which is a continuation-in-part of application No. 13/113,777, filed on May 23, 2011, now Pat. No. 9,867,975.

(56) References Cited

U.S. PATENT DOCUMENTS

| | | |
|---|---|---|
| 877,946 A | 2/1908 | Overton |
| 975,939 A | 11/1910 | William et al. |
| 1,445,642 A | 2/1923 | O'Neill |
| 1,793,068 A | 2/1931 | Dickinson |
| 2,098,340 A | 11/1937 | Henahan |
| 2,436,297 A | 2/1948 | Guarnaschelli |
| 2,457,052 A | 12/1948 | Le Clair |
| 2,771,644 A | 11/1956 | Martin |
| 3,262,448 A | 7/1966 | Ring et al. |
| 3,270,743 A | 9/1966 | Gingras |
| 3,301,392 A | 1/1967 | Eddingfield |
| 3,411,665 A | 11/1968 | Blum |
| 3,485,416 A | 12/1969 | Fohrman |
| 3,538,950 A | 11/1970 | Porteners |
| 3,595,241 A | 7/1971 | Sheridan |
| 3,604,582 A | 9/1971 | Boudin |
| 3,882,858 A | 5/1975 | Klemm |
| 3,977,401 A | 8/1976 | Pike |
| 3,977,517 A | 8/1976 | Kadlecik et al. |
| 3,987,930 A | 10/1976 | Fuson |
| 3,993,066 A | 11/1976 | Virag |
| 4,041,934 A | 8/1977 | Genese |
| 4,046,889 A | 9/1977 | Ondetti et al. |
| 4,052,511 A | 10/1977 | Cushman et al. |
| 4,053,052 A | 10/1977 | Jasper |
| 4,053,651 A | 10/1977 | Ondetti et al. |
| 4,078,686 A | 3/1978 | Karesh et al. |
| 4,095,810 A | 6/1978 | Kulle |
| 4,113,751 A | 9/1978 | Arnold |
| 4,129,571 A | 12/1978 | Ondetti et al. |
| 4,133,441 A | 1/1979 | Mittleman et al. |
| 4,154,840 A | 5/1979 | Ondetti et al. |
| 4,154,960 A | 5/1979 | Ondetti et al. |
| 4,192,443 A | 3/1980 | McLaren |
| 4,243,035 A | 1/1981 | Barrett |
| 4,264,664 A | 4/1981 | Kunz |
| 4,280,632 A | 7/1981 | Yuhara |
| 4,294,370 A | 10/1981 | Toeppen |
| 4,317,446 A | 3/1982 | Ambrosio et al. |
| 4,325,368 A | 4/1982 | Kaemmerer |
| 4,331,783 A | 5/1982 | Stoy |
| 4,335,756 A | 6/1982 | Sharp et al. |
| 4,337,327 A | 6/1982 | Stoy |
| 4,354,490 A | 10/1982 | Rogers |
| 4,369,294 A | 1/1983 | Stoy |
| 4,370,451 A | 1/1983 | Stoy |
| 4,379,874 A | 4/1983 | Stoy |
| 4,384,589 A | 5/1983 | Morris |
| 4,390,016 A | 6/1983 | Riess |
| 4,402,691 A | 9/1983 | Rosenthal et al. |
| 4,417,890 A | 11/1983 | Dennehey et al. |
| 4,420,589 A | 12/1983 | Stoy |
| 4,427,126 A | 1/1984 | Ostrowsky |
| 4,432,764 A | 2/1984 | Lopez |
| 4,432,766 A | 2/1984 | Bellotti et al. |
| 4,439,184 A | 3/1984 | Wheeler |
| 4,440,207 A | 4/1984 | Genatempo et al. |
| 4,444,310 A | 4/1984 | Odell |
| 4,446,967 A | 5/1984 | Halkyard |
| 4,447,419 A | 5/1984 | Quadro |
| 4,461,368 A | 7/1984 | Plourde |
| 4,461,896 A | 7/1984 | Portlock |
| 4,480,940 A | 11/1984 | Woodruff |
| 4,507,111 A | 3/1985 | Gordon et al. |
| 4,534,764 A | 8/1985 | Mittleman et al. |
| 4,559,043 A | 12/1985 | Whitehouse |
| 4,568,675 A | 2/1986 | Bush et al. |
| 4,585,758 A | 4/1986 | Huang et al. |
| 4,602,042 A | 7/1986 | Chantler et al. |
| 4,624,664 A | 11/1986 | Peluso et al. |
| 4,626,545 A | 12/1986 | Taub |
| 4,631,188 A | 12/1986 | Stoy |
| 4,642,091 A | 2/1987 | Richmond |
| 4,666,057 A | 5/1987 | Come et al. |
| 4,666,427 A | 5/1987 | Larsson et al. |
| 4,671,306 A | 6/1987 | Spector |
| 4,671,412 A | 6/1987 | Gatten |
| 4,681,886 A | 7/1987 | Haugwitz et al. |
| 4,692,458 A | 9/1987 | Ryan et al. |
| 4,692,459 A | 9/1987 | Ryan et al. |
| 4,703,762 A | 11/1987 | Rathbone et al. |
| 4,705,790 A | 11/1987 | Hubele et al. |
| 4,728,075 A | 3/1988 | Paradis |
| 4,728,321 A | 3/1988 | Chen |
| 4,738,668 A | 4/1988 | Bellotti et al. |
| 4,747,502 A | 5/1988 | Luenser |
| 4,748,160 A | 5/1988 | Bennion et al. |
| 4,752,983 A | 6/1988 | Grieshaber |
| 4,769,013 A | 9/1988 | Lorenz et al. |
| 4,778,447 A | 10/1988 | Velde et al. |
| 4,799,926 A | 1/1989 | Haber |
| 4,808,158 A | 2/1989 | Kreuzer et al. |
| 4,810,241 A | 3/1989 | Rogers |
| 4,811,847 A | 3/1989 | Reif et al. |
| 4,813,933 A | 3/1989 | Turner |
| 4,834,271 A | 5/1989 | Litwin |
| 4,874,366 A | 10/1989 | Zdeb et al. |
| 4,889,255 A | 12/1989 | Schiemann et al. |
| 4,894,056 A | 1/1990 | Bommarito |
| 4,898,580 A | 2/1990 | Crowley |
| 4,919,658 A | 4/1990 | Badia |
| 4,927,019 A | 5/1990 | Haber et al. |
| 4,941,873 A | 7/1990 | Fischer |
| 4,957,637 A | 9/1990 | Cornell |
| 4,963,132 A | 10/1990 | Gibson |
| 4,983,161 A | 1/1991 | Dadson et al. |
| 4,985,017 A | 1/1991 | Theeuwes |
| 4,989,733 A | 2/1991 | Patry |
| 4,991,629 A | 2/1991 | Ernesto et al. |
| 4,997,371 A | 3/1991 | Fischer |
| 4,999,210 A | 3/1991 | Solomon et al. |
| 5,002,964 A | 3/1991 | Loscalzo |
| 5,015,238 A | 5/1991 | Solomon et al. |
| 5,019,096 A | 5/1991 | Fox, Jr. et al. |
| 5,024,657 A | 6/1991 | Needham et al. |
| 5,025,001 A | 6/1991 | Loscalzo et al. |
| 5,026,359 A | 6/1991 | Burroughs |
| 5,031,622 A | 7/1991 | LaHaye |
| 5,033,961 A | 7/1991 | Kandler et al. |
| 5,049,139 A | 9/1991 | Gilchrist |
| 5,059,186 A | 10/1991 | Yamamoto et al. |
| 5,065,783 A | 11/1991 | Ogle, II |
| 5,071,413 A | 12/1991 | Utterberg |
| 5,129,824 A | 7/1992 | Keller |
| 5,143,104 A | 9/1992 | Iba et al. |
| 5,154,920 A | 10/1992 | Flesher et al. |
| 5,184,742 A | 2/1993 | DeCaprio et al. |
| 5,190,534 A | 3/1993 | Kendell |
| 5,195,957 A | 3/1993 | Tollini |
| 5,205,820 A | 4/1993 | Kriesel |
| 5,205,821 A | 4/1993 | Kruger et al. |
| 5,207,706 A | 5/1993 | Menaker |
| 5,212,204 A | 5/1993 | Keefer et al. |
| 5,240,675 A | 8/1993 | Wilk et al. |
| 5,242,421 A | 9/1993 | Chan |
| 5,242,425 A | 9/1993 | White et al. |
| 5,246,011 A | 9/1993 | Caillouette |
| 5,250,550 A | 10/1993 | Keefer et al. |
| D342,134 S | 12/1993 | Mongeon |
| 5,269,771 A | 12/1993 | Thomas et al. |
| 5,278,192 A | 1/1994 | Fung et al. |
| 5,297,310 A | 3/1994 | Cox et al. |
| 5,304,130 A | 4/1994 | Button |
| 5,324,647 A | 6/1994 | Rubens et al. |
| 5,330,426 A | 7/1994 | Kriesel et al. |
| 5,330,899 A | 7/1994 | Devaughn et al. |

(56) References Cited

U.S. PATENT DOCUMENTS

| | | |
|---|---|---|
| 5,337,730 A | 8/1994 | Maguire |
| 5,352,410 A | 10/1994 | Hansen et al. |
| 5,354,267 A | 10/1994 | Niermann et al. |
| 5,366,505 A | 11/1994 | Farber |
| 5,366,997 A | 11/1994 | Keefer et al. |
| 5,370,614 A | 12/1994 | Amundson et al. |
| 5,370,640 A | 12/1994 | Kolff |
| 5,375,589 A | 12/1994 | Bhatta |
| 5,380,758 A | 1/1995 | Stamler et al. |
| 5,405,919 A | 4/1995 | Keefer et al. |
| 5,407,807 A | 4/1995 | Markus |
| 5,409,012 A | 4/1995 | Sahatjian |
| 5,428,070 A | 6/1995 | Cooke et al. |
| 5,433,705 A | 7/1995 | Giebel et al. |
| 5,470,307 A | 11/1995 | Lindall |
| 5,471,706 A | 12/1995 | Wallock et al. |
| 5,496,288 A | 3/1996 | Sweeney |
| 5,485,827 A | 6/1996 | Zapol et al. |
| 5,525,357 A | 6/1996 | Keefer et al. |
| 5,536,241 A | 7/1996 | Zapol |
| 5,536,258 A | 7/1996 | Folden |
| 5,545,614 A | 8/1996 | Stamler et al. |
| 5,552,115 A | 9/1996 | Malchesky |
| 5,554,127 A | 9/1996 | Crouther et al. |
| 5,554,135 A | 9/1996 | Menyhay |
| 5,580,530 A | 12/1996 | Kowatsch et al. |
| 5,599,352 A | 2/1997 | Dinh et al. |
| 5,605,696 A | 2/1997 | Eury et al. |
| 5,607,072 A | 3/1997 | Rigney et al. |
| 5,620,088 A | 4/1997 | Martin et al. |
| 5,620,427 A | 4/1997 | Werschmidt et al. |
| 5,624,402 A | 4/1997 | Imbert |
| 5,628,733 A | 5/1997 | Zinreich et al. |
| 5,665,077 A | 9/1997 | Resen et al. |
| 5,685,835 A | 11/1997 | Brugger |
| 5,685,866 A | 11/1997 | Lopez |
| 5,688,253 A | 11/1997 | Lundquist |
| 5,694,978 A | 12/1997 | Heilmann et al. |
| 5,702,017 A | 12/1997 | Goncalves |
| 5,716,339 A | 2/1998 | Tanaka et al. |
| 5,722,537 A | 3/1998 | Sigler |
| 5,763,409 A | 6/1998 | Bayol et al. |
| 5,770,645 A | 6/1998 | Stamler et al. |
| 5,776,116 A | 7/1998 | Lopez |
| 5,782,808 A | 7/1998 | Folden |
| 5,792,120 A | 8/1998 | Menyhay |
| 5,797,887 A | 8/1998 | Rosen et al. |
| 5,810,792 A | 9/1998 | Fangrow, Jr. et al. |
| 5,814,666 A | 9/1998 | Green et al. |
| 5,820,604 A | 10/1998 | Fox et al. |
| 5,827,244 A | 10/1998 | Boettger |
| 5,839,715 A | 11/1998 | Leinsing |
| 5,902,631 A | 5/1999 | Wang et al. |
| 5,941,857 A | 8/1999 | Nguyen et al. |
| 5,947,296 A | 9/1999 | Castora |
| 5,951,519 A | 9/1999 | Utterberg |
| 5,954,957 A | 9/1999 | Chin-Loy et al. |
| 5,971,972 A | 10/1999 | Rosenbaum |
| D416,086 S | 11/1999 | Parris et al. |
| 5,989,229 A | 11/1999 | Chiappetta |
| 5,994,444 A | 11/1999 | Trescony |
| 5,996,779 A | 12/1999 | Klardie et al. |
| 6,041,805 A | 3/2000 | Gydesen et al. |
| 6,045,539 A | 4/2000 | Menyhay |
| 6,045,623 A | 4/2000 | Cannon |
| 6,059,107 A | 5/2000 | Nosted et al. |
| 6,068,475 A | 5/2000 | Stoyka, Jr. et al. |
| 6,071,413 A | 6/2000 | Dyke |
| 6,087,479 A | 7/2000 | Stamler et al. |
| 6,093,743 A | 7/2000 | Lai et al. |
| 6,095,356 A | 8/2000 | Rits |
| 6,105,812 A | 8/2000 | Riordan |
| 6,116,468 A | 9/2000 | Nilson |
| 6,117,114 A | 9/2000 | Paradis |
| 6,126,640 A | 10/2000 | Tucker et al. |
| 6,143,318 A | 11/2000 | Gilchrist et al. |
| 6,146,363 A | 11/2000 | Giebel et al. |
| 6,152,913 A | 11/2000 | Feith et al. |
| 6,158,614 A | 12/2000 | Haines et al. |
| 6,170,522 B1 | 1/2001 | Tanida |
| 6,171,287 B1 | 1/2001 | Lynn et al. |
| 6,174,539 B1 | 1/2001 | Stamler et al. |
| 6,179,141 B1 | 1/2001 | Nakamura |
| 6,183,450 B1 | 2/2001 | Lois |
| 6,190,364 B1 | 2/2001 | Imbert |
| 6,202,870 B1 | 3/2001 | Pearce |
| 6,202,901 B1 | 3/2001 | Gerber et al. |
| 6,206,134 B1 | 3/2001 | Stark et al. |
| 6,207,855 B1 | 3/2001 | Toone et al. |
| 6,227,391 B1 | 5/2001 | King |
| 6,232,406 B1 | 5/2001 | Stoy |
| 6,232,434 B1 | 5/2001 | Stamler et al. |
| 6,237,800 B1 | 5/2001 | Barrett et al. |
| 6,245,056 B1 | 6/2001 | Walker et al. |
| 6,248,380 B1 | 6/2001 | Kocher et al. |
| 6,250,315 B1 | 6/2001 | Ernster |
| 6,255,277 B1 | 7/2001 | Stamler et al. |
| 6,315,113 B1 | 11/2001 | Britton et al. |
| 6,315,761 B1 | 11/2001 | Shcherbina et al. |
| 6,359,167 B2 | 3/2002 | Toone et al. |
| 6,359,182 B1 | 3/2002 | Stamler et al. |
| 6,379,660 B1 | 4/2002 | Saavedra et al. |
| 6,379,691 B1 | 4/2002 | Tedeschi et al. |
| 6,394,983 B1 | 5/2002 | Mayoral et al. |
| 6,402,207 B1 | 6/2002 | Segal et al. |
| 6,403,759 B2 | 6/2002 | Stamler et al. |
| 6,409,716 B1 | 6/2002 | Sahatjian et al. |
| 6,444,318 B1 | 9/2002 | Guire et al. |
| 6,468,259 B1 | 10/2002 | Djokic et al. |
| 6,471,978 B1 | 10/2002 | Stamler et al. |
| 6,488,951 B2 | 12/2002 | Toone et al. |
| 6,491,965 B1 | 12/2002 | Berry et al. |
| 6,538,116 B2 | 3/2003 | Stamler et al. |
| 6,550,493 B2 | 4/2003 | Williamson et al. |
| 6,555,504 B1 | 4/2003 | Ayai et al. |
| 6,562,781 B1 | 5/2003 | Berry et al. |
| 6,583,311 B2 | 6/2003 | Toone et al. |
| 6,585,691 B1 | 7/2003 | Vitello |
| 6,605,294 B2 | 8/2003 | Sawhney |
| 6,605,751 B1 | 8/2003 | Gibbins et al. |
| 6,632,199 B1 | 10/2003 | Tucker et al. |
| 6,634,498 B2 | 10/2003 | Kayerod et al. |
| 6,656,217 B1 | 12/2003 | Herzog, Jr. et al. |
| 6,673,891 B2 | 1/2004 | Stamler et al. |
| 6,679,395 B1 | 1/2004 | Pfefferkorn et al. |
| 6,679,870 B1 | 1/2004 | Finch et al. |
| 6,681,803 B2 | 1/2004 | Taneya et al. |
| 6,685,694 B2 | 2/2004 | Finch et al. |
| 6,692,468 B1 | 2/2004 | Waldenburg |
| 6,716,396 B1 | 4/2004 | Anderson |
| 6,725,492 B2 | 4/2004 | Moore et al. |
| 6,786,884 B1 | 9/2004 | DeCant, Jr. et al. |
| 6,808,510 B1 | 10/2004 | DiFiore |
| 6,827,766 B2 | 12/2004 | Carnes et al. |
| 6,871,087 B1 | 3/2005 | Hughes et al. |
| 6,875,840 B2 | 4/2005 | Stamler et al. |
| 6,880,706 B2 | 4/2005 | Braconnot et al. |
| 6,887,994 B2 | 5/2005 | Stamler et al. |
| 6,911,025 B2 | 6/2005 | Miyahar |
| 6,929,005 B2 | 8/2005 | Sullivan et al. |
| 6,943,035 B1 | 9/2005 | Davies et al. |
| 7,015,347 B2 | 3/2006 | Toone et al. |
| 7,030,238 B2 | 4/2006 | Stamler et al. |
| 7,045,585 B2 | 5/2006 | Berry et al. |
| 7,049,308 B2 | 5/2006 | Stamler et al. |
| 7,052,711 B2 | 5/2006 | West et al. |
| 7,056,308 B2 | 6/2006 | Utterberg |
| 7,067,659 B2 | 6/2006 | Stamler et al. |
| 7,081,109 B2 | 7/2006 | Tighe et al. |
| 7,083,605 B2 | 8/2006 | Miyahara |
| 7,087,709 B2 | 8/2006 | Stamler et al. |
| 7,097,850 B2 | 8/2006 | Chappa et al. |
| 7,147,625 B2 | 12/2006 | Sarangapani et al. |
| 7,160,272 B1 | 1/2007 | Eyal et al. |

(56) References Cited

U.S. PATENT DOCUMENTS

| | | | |
|---|---|---|---|
| 7,195,615 B2 | 3/2007 | Tan |
| 7,198,611 B2 | 4/2007 | Connell et al. |
| 7,259,250 B2 | 8/2007 | Stamler et al. |
| 7,279,176 B1 | 10/2007 | West et al. |
| 7,282,186 B2 | 10/2007 | Lake, Jr. et al. |
| 7,309,326 B2 | 12/2007 | Fangrow, Jr. |
| 7,316,669 B2 | 1/2008 | Ranalletta |
| 7,347,853 B2 | 3/2008 | DiFiore et al. |
| 7,417,109 B2 | 8/2008 | Stamler et al. |
| 7,431,712 B2 | 10/2008 | Kim |
| 7,442,402 B2 | 10/2008 | Chudzik et al. |
| 7,452,349 B2 | 11/2008 | Miyahar |
| 7,485,107 B2 | 2/2009 | DiFiore et al. |
| 7,491,192 B2 | 2/2009 | DiFiore et al. |
| 7,516,846 B2 | 4/2009 | Hansen |
| 7,611,505 B2 | 11/2009 | Ranalletta et al. |
| 7,614,426 B2 | 11/2009 | Kitani et al. |
| 7,615,034 B2 | 11/2009 | DiFiore |
| 7,625,907 B2 | 12/2009 | Stamler et al. |
| 7,635,344 B2 | 12/2009 | Tennican et al. |
| D607,325 S | 1/2010 | Rogers et al. |
| 7,708,714 B2 | 5/2010 | Connell et al. |
| 7,731,678 B2 | 6/2010 | Tennican et al. |
| 7,731,679 B2 | 6/2010 | Tennican et al. |
| 7,749,189 B2 | 7/2010 | Tennican et al. |
| 7,753,891 B2 | 7/2010 | Tennican et al. |
| 7,758,530 B2 | 7/2010 | DiFiore et al. |
| 7,762,524 B2 | 7/2010 | Cawthon et al. |
| 7,763,006 B2 | 7/2010 | Tennican |
| 7,766,182 B2 | 8/2010 | Trent et al. |
| 7,766,897 B2 | 8/2010 | Ramsey et al. |
| 7,776,011 B2 | 8/2010 | Tennican et al. |
| 7,780,794 B2 | 8/2010 | Rogers et al. |
| 7,785,616 B2 | 8/2010 | Stamler et al. |
| 7,794,675 B2 | 9/2010 | Lynn |
| 7,799,010 B2 | 9/2010 | Tennican |
| 7,815,614 B2 | 10/2010 | Fangrow, Jr. |
| 7,857,793 B2 | 12/2010 | Raulerson et al. |
| 7,922,701 B2 | 4/2011 | Buchman |
| 7,922,711 B2 | 4/2011 | Ranalletta et al. |
| 7,928,079 B2 | 4/2011 | Hrabie et al. |
| 7,938,795 B2 | 5/2011 | DiFiore et al. |
| 7,956,062 B2 | 6/2011 | Stamler et al. |
| 7,959,026 B2 | 6/2011 | Bertani |
| 7,963,565 B2 | 6/2011 | Suter |
| 7,972,137 B2 | 7/2011 | Rosen |
| 7,972,322 B2 | 7/2011 | Tennican |
| 7,981,090 B2 | 7/2011 | Plishka et al. |
| 7,985,302 B2 | 7/2011 | Rogers et al. |
| 7,993,309 B2 | 8/2011 | Schweikert |
| 8,034,454 B2 | 10/2011 | Terry |
| 8,065,773 B2 | 11/2011 | Vaillancourt et al. |
| 8,066,670 B2 | 11/2011 | Cluff et al. |
| 8,069,523 B2 | 12/2011 | Vaillancourt et al. |
| 8,113,837 B2 | 2/2012 | Zegarelli |
| 8,146,757 B2 | 4/2012 | Abreu et al. |
| 8,162,899 B2 | 4/2012 | Tennican |
| 8,167,847 B2 | 5/2012 | Anderson et al. |
| 8,172,825 B2 | 5/2012 | Solomon et al. |
| 8,177,761 B2 | 5/2012 | Howlett et al. |
| 8,197,749 B2 | 6/2012 | Howlett et al. |
| 8,206,514 B2 | 6/2012 | Rogers et al. |
| 8,231,587 B2 | 7/2012 | Solomon et al. |
| 8,231,602 B2 | 7/2012 | Anderson et al. |
| 8,252,247 B2 | 8/2012 | Ferlic |
| 8,262,628 B2 | 9/2012 | Fangrow, Jr. |
| 8,262,643 B2 | 9/2012 | Tennican |
| 8,273,303 B2 | 9/2012 | Ferlic et al. |
| 8,281,824 B2 | 10/2012 | Molema et al. |
| 8,328,767 B2 | 12/2012 | Solomon et al. |
| 8,336,152 B2 | 12/2012 | Kerr et al. |
| 8,343,112 B2 | 1/2013 | Solomon et al. |
| 8,361,408 B2 | 1/2013 | Lynn |
| 8,372,045 B2 | 2/2013 | Needle et al. |
| 8,377,040 B2 | 2/2013 | Burkholz et al. |
| 8,414,547 B2 | 4/2013 | DiFiore et al. |
| 8,419,713 B1 | 4/2013 | Solomon et al. |
| 8,454,579 B2 | 6/2013 | Fangrow, Jr. |
| 8,480,968 B2 | 7/2013 | Lynn |
| 8,491,546 B2 | 7/2013 | Hoang et al. |
| 8,500,717 B2 | 8/2013 | Becker |
| 8,506,527 B2 | 8/2013 | Carlyon |
| 8,506,538 B2 | 8/2013 | Chelak |
| 8,523,798 B2 | 9/2013 | DiFiore |
| 8,523,830 B2 | 9/2013 | Solomon et al. |
| 8,523,831 B2 | 9/2013 | Solomon et al. |
| 8,533,887 B2 | 9/2013 | Hirst |
| 8,545,479 B2 | 10/2013 | Kitani et al. |
| 8,568,371 B2 | 10/2013 | Siopes et al. |
| 8,622,995 B2 | 1/2014 | Ziebol et al. |
| 8,622,996 B2 | 1/2014 | Ziebol et al. |
| 8,641,681 B2 | 2/2014 | Solomon et al. |
| 8,641,684 B2 | 2/2014 | Utterberg et al. |
| 8,647,308 B2 | 2/2014 | Solomon et al. |
| 8,647,326 B2 | 2/2014 | Solomon et al. |
| 8,651,271 B1 | 2/2014 | Shen |
| 8,671,496 B2 | 3/2014 | Kerr et al. |
| 8,740,864 B2 | 6/2014 | Hoang et al. |
| 8,777,504 B2 | 7/2014 | Shaw et al. |
| 8,791,073 B2 | 7/2014 | West et al. |
| 8,845,593 B2 | 9/2014 | Anderson et al. |
| 8,877,231 B2 | 11/2014 | Rosen |
| 8,910,919 B2 | 12/2014 | Bonnal et al. |
| 8,920,404 B2 | 12/2014 | DiFiore et al. |
| 8,968,268 B2 | 3/2015 | Anderson et al. |
| 8,981,139 B2 | 3/2015 | Schoenfisch et al. |
| 8,999,073 B2 | 4/2015 | Rogers et al. |
| 9,022,984 B2 | 5/2015 | Ziebol et al. |
| 9,072,296 B2 | 7/2015 | Mills et al. |
| 9,072,868 B2 | 7/2015 | Ziebol et al. |
| 9,078,992 B2 | 7/2015 | Ziebol et al. |
| 9,089,680 B2 | 7/2015 | Ueda et al. |
| 9,095,667 B2 | 8/2015 | Von Schuckmann |
| 9,101,685 B2 | 8/2015 | Li et al. |
| 9,101,750 B2 | 8/2015 | Solomon et al. |
| 9,114,915 B2 | 8/2015 | Solomon et al. |
| 9,125,600 B2 | 9/2015 | Steube et al. |
| 9,149,624 B2 | 10/2015 | Lewis |
| 9,180,252 B2 | 11/2015 | Gelblum et al. |
| 9,192,449 B2 | 11/2015 | Kerr et al. |
| 9,205,248 B2 | 12/2015 | Wu et al. |
| 9,216,440 B2 | 12/2015 | Ma et al. |
| 9,242,084 B2 | 1/2016 | Solomon et al. |
| 9,248,093 B2 | 2/2016 | Kelley, III et al. |
| 9,248,229 B2 | 2/2016 | Devouassoux et al. |
| 9,259,284 B2 | 2/2016 | Rogers et al. |
| 9,259,535 B2 | 2/2016 | Anderson et al. |
| 9,283,367 B2 | 3/2016 | Hoang et al. |
| 9,283,368 B2 | 3/2016 | Hoang et al. |
| 9,283,369 B2 | 3/2016 | Ma et al. |
| 9,289,588 B2 | 3/2016 | Chen |
| 9,296,525 B2 | 3/2016 | Murphy et al. |
| 9,302,049 B2 | 4/2016 | Tekeste |
| 9,320,858 B2 | 4/2016 | Grimm et al. |
| 9,320,859 B2 | 4/2016 | Grimm et al. |
| 9,320,860 B2 | 4/2016 | Grimm et al. |
| 9,352,080 B2 | 5/2016 | Goodall et al. |
| 9,352,140 B2 | 5/2016 | Kerr et al. |
| 9,352,141 B2 | 5/2016 | Wong |
| 9,352,142 B2 | 5/2016 | Ziebol et al. |
| 9,381,339 B2 | 7/2016 | Wu et al. |
| 9,399,125 B2 | 7/2016 | Burkholz |
| 9,408,971 B2 | 8/2016 | Carlyon |
| 9,527,660 B2 | 12/2016 | Tennican |
| 9,592,375 B2 | 3/2017 | Tennican |
| 9,700,676 B2 | 7/2017 | Anderson et al. |
| 9,700,677 B2 | 7/2017 | Anderson et al. |
| 9,700,710 B2 | 7/2017 | Anderson et al. |
| 9,707,348 B2 | 7/2017 | Anderson et al. |
| 9,707,349 B2 | 7/2017 | Anderson et al. |
| 9,707,350 B2 | 7/2017 | Anderson et al. |
| 9,809,355 B2 | 11/2017 | Solomon et al. |
| 9,849,276 B2 | 12/2017 | Ziebol et al. |
| 9,867,975 B2 | 1/2018 | Gardner et al. |

(56) References Cited

U.S. PATENT DOCUMENTS

| | | |
|---|---|---|
| 9,907,617 B2 | 3/2018 | Rogers |
| 9,933,094 B2 | 4/2018 | Fangrow |
| 9,999,471 B2 | 6/2018 | Rogers et al. |
| 10,016,587 B2 | 7/2018 | Gardner et al. |
| 10,046,156 B2 | 8/2018 | Gardner et al. |
| 10,159,829 B2 | 12/2018 | Ziebol et al. |
| 10,166,381 B2 * | 1/2019 | Gardner ............... A61M 39/20 |
| 10,195,000 B2 | 2/2019 | Rogers et al. |
| 10,201,692 B2 | 2/2019 | Chang |
| 10,328,207 B2 | 6/2019 | Anderson et al. |
| 10,524,982 B2 | 1/2020 | Fangrow |
| 10,525,250 B1 | 1/2020 | Ziebol et al. |
| 10,695,550 B2 | 6/2020 | Gardner et al. |
| 10,744,316 B2 | 8/2020 | Fangrow |
| 10,806,919 B2 * | 10/2020 | Gardner ............... A61M 39/20 |
| 10,821,278 B2 | 11/2020 | Gardner et al. |
| 11,160,932 B2 | 11/2021 | Anderson et al. |
| 11,229,746 B2 | 1/2022 | Anderson et al. |
| 11,351,353 B2 | 6/2022 | Ziebol et al. |
| 11,389,634 B2 | 7/2022 | Ziebol et al. |
| 11,400,195 B2 | 8/2022 | Ziebol et al. |
| 11,433,215 B2 | 9/2022 | Ziebol et al. |
| 11,497,904 B2 | 11/2022 | Fangrow et al. |
| 11,517,732 B2 | 12/2022 | Ziebol et al. |
| 11,517,733 B2 | 12/2022 | Fangrow |
| 11,534,595 B2 | 12/2022 | Ziebol et al. |
| 11,541,220 B2 | 1/2023 | Ziebol et al. |
| 11,541,221 B2 | 1/2023 | Ziebol et al. |
| 11,559,467 B2 | 1/2023 | Fangrow |
| 11,684,720 B2 | 6/2023 | Anderson et al. |
| 11,826,539 B2 | 11/2023 | Ziebol et al. |
| 2002/0010438 A1 | 1/2002 | Finch et al. |
| 2002/0077693 A1 | 6/2002 | Barclay et al. |
| 2002/0082682 A1 | 6/2002 | Barclay et al. |
| 2002/0098278 A1 | 7/2002 | Bates et al. |
| 2002/0193752 A1 | 12/2002 | Lynn |
| 2003/0039697 A1 | 2/2003 | Zhao et al. |
| 2003/0060749 A1 | 3/2003 | Aneas |
| 2003/0062376 A1 | 4/2003 | Sears et al. |
| 2003/0072783 A1 | 4/2003 | Stamler et al. |
| 2003/0153865 A1 | 8/2003 | Connell et al. |
| 2003/0199835 A1 | 10/2003 | Leinsing et al. |
| 2004/0034042 A1 | 2/2004 | Tsuji et al. |
| 2004/0034329 A1 | 2/2004 | Mankus et al. |
| 2004/0037836 A1 | 2/2004 | Stamler et al. |
| 2004/0048542 A1 | 3/2004 | Thomaschefsky et al. |
| 2004/0052689 A1 | 3/2004 | Yao |
| 2004/0052831 A1 | 3/2004 | Modak et al. |
| 2004/0156908 A1 | 8/2004 | Polaschegg et al. |
| 2004/0210201 A1 | 10/2004 | Farnan |
| 2004/0215148 A1 | 10/2004 | Hwang et al. |
| 2004/0247640 A1 | 12/2004 | Zhao et al. |
| 2004/0249337 A1 | 12/2004 | DiFiore |
| 2004/0249338 A1 | 12/2004 | DeCant, Jr. et al. |
| 2004/0258560 A1 | 12/2004 | Lake, Jr. et al. |
| 2005/0013836 A1 | 1/2005 | Raad |
| 2005/0065479 A1 | 3/2005 | Schiller et al. |
| 2005/0098527 A1 | 5/2005 | Yates et al. |
| 2005/0124970 A1 | 6/2005 | Kunin et al. |
| 2005/0147524 A1 | 7/2005 | Bousquet |
| 2005/0147525 A1 | 7/2005 | Bousquet |
| 2005/0148930 A1 | 7/2005 | Hseih et al. |
| 2005/0152891 A1 | 7/2005 | Toone et al. |
| 2005/0171493 A1 | 8/2005 | Nicholls |
| 2005/0203460 A1 | 9/2005 | Kim |
| 2005/0214185 A1 | 9/2005 | Castaneda |
| 2005/0220882 A1 | 10/2005 | Pritchard et al. |
| 2005/0228482 A1 | 10/2005 | Herzog et al. |
| 2005/0256461 A1 | 11/2005 | DiFiore et al. |
| 2005/0265958 A1 | 12/2005 | West et al. |
| 2005/0267421 A1 | 12/2005 | Wing |
| 2005/0271711 A1 | 12/2005 | Lynch et al. |
| 2005/0288551 A1 | 12/2005 | Callister et al. |
| 2006/0004316 A1 | 1/2006 | DiFiore et al. |
| 2006/0024372 A1 | 2/2006 | Utterberg et al. |
| 2006/0030827 A1 | 2/2006 | Raulerson et al. |
| 2006/0096348 A1 | 5/2006 | DiFiore |
| 2006/0118122 A1 | 6/2006 | Martens et al. |
| 2006/0149191 A1 | 7/2006 | DiFiore |
| 2006/0195117 A1 | 8/2006 | Rucker et al. |
| 2006/0206178 A1 | 9/2006 | Kim |
| 2006/0261076 A1 | 11/2006 | Anderson |
| 2007/0003603 A1 | 1/2007 | Karandikar et al. |
| 2007/0106205 A1 | 5/2007 | Connell et al. |
| 2007/0112333 A1 | 5/2007 | Hoang et al. |
| 2007/0156118 A1 | 7/2007 | Ramsey et al. |
| 2007/0167910 A1 | 7/2007 | Tennican et al. |
| 2007/0176117 A1 | 8/2007 | Redmond et al. |
| 2007/0187353 A1 | 8/2007 | Fox et al. |
| 2007/0212381 A1 | 9/2007 | DiFiore et al. |
| 2007/0231315 A1 | 10/2007 | Lichte et al. |
| 2007/0248676 A1 | 10/2007 | Stamler et al. |
| 2007/0249996 A1 | 10/2007 | Tennican et al. |
| 2007/0265578 A1 | 11/2007 | Tennican et al. |
| 2007/0282280 A1 | 12/2007 | Tennican |
| 2007/0287989 A1 | 12/2007 | Crawford et al. |
| 2008/0019889 A1 | 1/2008 | Rogers et al. |
| 2008/0027399 A1 | 1/2008 | Harding et al. |
| 2008/0027401 A1 | 1/2008 | Ou-Yang |
| 2008/0033371 A1 | 2/2008 | Updegraff et al. |
| 2008/0039803 A1 | 2/2008 | Lynn |
| 2008/0058733 A1 | 3/2008 | Vogt et al. |
| 2008/0086091 A1 | 4/2008 | Anderson et al. |
| 2008/0093245 A1 | 4/2008 | Periasamy et al. |
| 2008/0095680 A1 | 4/2008 | Steffens et al. |
| 2008/0097315 A1 | 4/2008 | Miner et al. |
| 2008/0097407 A1 | 4/2008 | Plishka |
| 2008/0287920 A1 | 5/2008 | Fangrow et al. |
| 2008/0014005 A1 | 6/2008 | Shirley |
| 2008/0128646 A1 | 6/2008 | Clawson |
| 2008/0132880 A1 | 6/2008 | Buchman |
| 2008/0147047 A1 | 6/2008 | Davis et al. |
| 2008/0161763 A1 | 7/2008 | Harding et al. |
| 2008/0172007 A1 | 7/2008 | Bousquet |
| 2008/0173651 A1 | 7/2008 | Ping |
| 2008/0177250 A1 | 7/2008 | Howlett et al. |
| 2008/0187460 A1 | 8/2008 | Utterberg et al. |
| 2008/0188791 A1 | 8/2008 | DiFiore et al. |
| 2008/0235888 A1 | 10/2008 | Vaillancourt et al. |
| 2008/0262465 A1 | 10/2008 | Zinger et al. |
| 2008/0318333 A1 | 12/2008 | Nielsen et al. |
| 2008/0319423 A1 | 12/2008 | Tanghoj et al. |
| 2009/0008393 A1 | 1/2009 | Howlett et al. |
| 2009/0012426 A1 | 1/2009 | Tennican |
| 2009/0024096 A1 | 1/2009 | Hai et al. |
| 2009/0028750 A1 | 1/2009 | Ryan |
| 2009/0062766 A1 | 3/2009 | Howlett et al. |
| 2009/0093757 A1 | 4/2009 | Tennican |
| 2009/0099529 A1 * | 4/2009 | Anderson ............. A61M 39/20 |
| | | 604/192 |
| 2009/0126867 A1 | 5/2009 | Decant, Jr. et al. |
| 2009/0137969 A1 | 5/2009 | Colantonio et al. |
| 2009/0149820 A1 | 6/2009 | DiFiore |
| 2009/0163876 A1 | 6/2009 | Chebator et al. |
| 2009/0205151 A1 | 8/2009 | Fisher et al. |
| 2009/0205656 A1 | 8/2009 | Nishibayashi et al. |
| 2009/0247485 A1 | 10/2009 | Ahmed et al. |
| 2009/0259194 A1 | 10/2009 | Pinedjian et al. |
| 2009/0270832 A1 | 10/2009 | Vancaillie et al. |
| 2009/0293882 A1 | 12/2009 | Terry |
| 2010/0003067 A1 | 1/2010 | Shaw et al. |
| 2010/0004510 A1 | 1/2010 | Kuroshima |
| 2010/0047123 A1 | 2/2010 | Solomon et al. |
| 2010/0049170 A1 | 2/2010 | Solomon et al. |
| 2010/0050351 A1 * | 3/2010 | Colantonio ............... A61L 2/18 |
| | | 15/104.93 |
| 2010/0059474 A1 | 3/2010 | Brandenburger et al. |
| 2010/0064456 A1 * | 3/2010 | Ferlic ....................... A61L 2/16 |
| | | 15/210.1 |
| 2010/0074932 A1 | 3/2010 | Talsma |
| 2010/0106102 A1 | 4/2010 | Ziebol et al. |
| 2010/0106103 A1 | 4/2010 | Ziebol et al. |
| 2010/0137472 A1 | 6/2010 | Ou-Yang |
| 2010/0143427 A1 | 6/2010 | King et al. |

(56) References Cited

U.S. PATENT DOCUMENTS

| | | |
|---|---|---|
| 2010/0152670 A1 | 6/2010 | Low |
| 2010/0160894 A1 | 6/2010 | Julian et al. |
| 2010/0172794 A1 | 7/2010 | Ferlic et al. |
| 2010/0242993 A1 | 9/2010 | Hoang et al. |
| 2010/0253070 A1 | 10/2010 | Cheon et al. |
| 2010/0280805 A1 | 11/2010 | DiFiore |
| 2010/0292673 A1 | 11/2010 | Korogi et al. |
| 2010/0292674 A1 | 11/2010 | Jepson et al. |
| 2010/0306938 A1 | 12/2010 | Rogers et al. |
| 2010/0318040 A1 | 12/2010 | Kelley, III et al. |
| 2011/0030726 A1 | 2/2011 | Vaillancourt et al. |
| 2011/0044850 A1 | 2/2011 | Solomon et al. |
| 2011/0046564 A1 | 2/2011 | Zhong |
| 2011/0046603 A1 | 2/2011 | Felsovalyi et al. |
| 2011/0062703 A1 | 3/2011 | Lopez |
| 2011/0064512 A1 | 3/2011 | Shaw et al. |
| 2011/0071475 A1 | 3/2011 | Horvath et al. |
| 2011/0082431 A1 | 4/2011 | Burgess et al. |
| 2011/0150958 A1 | 6/2011 | Davis et al. |
| 2011/0184338 A1 | 7/2011 | McKay |
| 2011/0184382 A1 | 7/2011 | Cady |
| 2011/0208128 A1 | 8/2011 | Wu et al. |
| 2011/0217212 A1 | 9/2011 | Solomon et al. |
| 2011/0232020 A1 | 9/2011 | Rogers et al. |
| 2011/0265825 A1 | 11/2011 | Rogers et al. |
| 2011/0276031 A1 | 11/2011 | Hoang et al. |
| 2011/0277788 A1 | 11/2011 | Rogers et al. |
| 2011/0282302 A1 | 11/2011 | Lopez et al. |
| 2011/0290799 A1 | 12/2011 | Anderson et al. |
| 2011/0311602 A1 | 12/2011 | Mills et al. |
| 2011/0314619 A1 | 12/2011 | Schweikert |
| 2012/0022469 A1 | 1/2012 | Albert et al. |
| 2012/0029483 A1 | 2/2012 | Griffith et al. |
| 2012/0031904 A1 | 2/2012 | Kuhn et al. |
| 2012/0039764 A1 | 2/2012 | Solomon et al. |
| 2012/0083730 A1 | 4/2012 | Rush et al. |
| 2012/0083750 A1 | 4/2012 | Sansoucy |
| 2012/0157965 A1 | 6/2012 | Wotton et al. |
| 2012/0191029 A1 | 7/2012 | Hopf et al. |
| 2012/0191067 A1 | 7/2012 | Chia et al. |
| 2012/0195807 A1 | 8/2012 | Ferlic |
| 2012/0216359 A1 | 8/2012 | Rogers et al. |
| 2012/0216360 A1 | 8/2012 | Rogers et al. |
| 2012/0220955 A1 | 8/2012 | Maseda et al. |
| 2012/0283693 A1 | 11/2012 | Anderson et al. |
| 2012/0283696 A1 | 11/2012 | Cronenberg et al. |
| 2012/0296284 A1 | 11/2012 | Anderson et al. |
| 2012/0302968 A1 | 11/2012 | Tennican |
| 2012/0302970 A1 | 11/2012 | Tennican |
| 2012/0302997 A1 | 11/2012 | Gardner et al. |
| 2012/0315201 A1 | 12/2012 | Ferlic et al. |
| 2013/0030414 A1 | 1/2013 | Gardner et al. |
| 2013/0035667 A1 | 2/2013 | Anderson et al. |
| 2013/0039953 A1 | 2/2013 | Dudnyk et al. |
| 2013/0053751 A1 | 2/2013 | Holtham |
| 2013/0072908 A1 | 3/2013 | Solomon et al. |
| 2013/0085313 A1 | 4/2013 | Fowler et al. |
| 2013/0085474 A1 | 4/2013 | Charles et al. |
| 2013/0098398 A1 | 4/2013 | Kerr et al. |
| 2013/0098938 A1 | 4/2013 | Efthimiadis |
| 2013/0102950 A1 | 4/2013 | DiFiore |
| 2013/0123754 A1 | 5/2013 | Solomon et al. |
| 2013/0134161 A1 | 5/2013 | Fogel et al. |
| 2013/0138085 A1 | 5/2013 | Tennican |
| 2013/0144258 A1 | 6/2013 | Ziebol et al. |
| 2013/0150795 A1 | 6/2013 | Snow |
| 2013/0164189 A1 | 6/2013 | Hadden |
| 2013/0171030 A1 | 7/2013 | Ferlic et al. |
| 2013/0183635 A1 | 7/2013 | Wilhoit |
| 2013/0184679 A1 | 7/2013 | Ziebol et al. |
| 2013/0204231 A1 | 8/2013 | Ziebol et al. |
| 2013/0274686 A1 | 10/2013 | Ziebol et al. |
| 2014/0034540 A1 | 2/2014 | Solomon et al. |
| 2014/0042116 A1 | 2/2014 | Shen et al. |
| 2014/0048079 A1 | 2/2014 | Gardner et al. |
| 2014/0052074 A1 | 2/2014 | Tekeste |
| 2014/0101876 A1 | 4/2014 | Rogers et al. |
| 2014/0148781 A1 | 5/2014 | Tekeste |
| 2014/0155868 A1 | 6/2014 | Nelson et al. |
| 2014/0227144 A1 | 8/2014 | Liu et al. |
| 2014/0228775 A1 | 8/2014 | Burkholz et al. |
| 2014/0228809 A1 | 8/2014 | Wong |
| 2014/0243797 A1 | 8/2014 | Jensen et al. |
| 2014/0336610 A1 | 11/2014 | Michel et al. |
| 2015/0018774 A1 | 1/2015 | Anderson et al. |
| 2015/0086441 A1 | 3/2015 | She et al. |
| 2015/0165127 A1 | 6/2015 | Haefele et al. |
| 2015/0217106 A1 | 8/2015 | Banik et al. |
| 2015/0237854 A1 | 8/2015 | Mills et al. |
| 2015/0238703 A1 | 8/2015 | Glocker |
| 2015/0258324 A1 | 9/2015 | Chida et al. |
| 2015/0298893 A1 | 10/2015 | Welp |
| 2015/0306367 A1 | 10/2015 | DiFiore |
| 2015/0314119 A1 | 11/2015 | Anderson et al. |
| 2015/0314120 A1 | 11/2015 | Gardner et al. |
| 2015/0320926 A1 | 11/2015 | Fitzpatrick et al. |
| 2015/0320992 A1 | 11/2015 | Bonnet et al. |
| 2015/0343174 A1 | 12/2015 | Ziebol et al. |
| 2015/0374968 A1 | 12/2015 | Solomon et al. |
| 2016/0001056 A1 | 1/2016 | Nelson et al. |
| 2016/0001058 A1 | 1/2016 | Ziebol et al. |
| 2016/0015863 A1 | 1/2016 | Gupta et al. |
| 2016/0015931 A1 | 1/2016 | Ryan et al. |
| 2016/0015959 A1 | 1/2016 | Solomon et al. |
| 2016/0045629 A1 | 2/2016 | Gardner et al. |
| 2016/0067365 A1 | 3/2016 | Ma et al. |
| 2016/0067471 A1 | 3/2016 | Ingram et al. |
| 2016/0088995 A1 | 3/2016 | Ueda et al. |
| 2016/0089530 A1 | 3/2016 | Sathe |
| 2016/0101223 A1 | 4/2016 | Kelley, III et al. |
| 2016/0101276 A1 | 4/2016 | Tekeste |
| 2016/0106969 A1 | 4/2016 | Neftel |
| 2016/0121097 A1 | 5/2016 | Steele |
| 2016/0144118 A1 | 5/2016 | Solomon et al. |
| 2016/0158520 A1 | 6/2016 | Ma et al. |
| 2016/0158521 A1 | 6/2016 | Hoang et al. |
| 2016/0158522 A1 | 6/2016 | Hoang et al. |
| 2016/0184527 A1 | 6/2016 | Tekeste |
| 2016/0213912 A1 | 7/2016 | Daneluzzi |
| 2016/0220790 A1 | 8/2016 | Borowicz |
| 2016/0250420 A1 | 9/2016 | Maritan et al. |
| 2016/0354596 A1 | 12/2016 | DiFiore |
| 2017/0020911 A1 | 1/2017 | Berry et al. |
| 2017/0042636 A1 | 2/2017 | Young |
| 2017/0143447 A1 | 5/2017 | Rogers et al. |
| 2017/0182241 A1 | 6/2017 | DiFiore |
| 2017/0203092 A1 | 7/2017 | Ryan et al. |
| 2017/0239443 A1 | 8/2017 | Abitabilo et al. |
| 2017/0361023 A1 | 12/2017 | Anderson et al. |
| 2018/0200500 A1 | 7/2018 | Ziebol et al. |
| 2018/0214684 A1 | 8/2018 | Avula et al. |
| 2018/0369562 A1 | 12/2018 | Gardner |
| 2019/0038888 A1 | 2/2019 | Gardner |
| 2019/0111245 A1 | 4/2019 | Gardner et al. |
| 2019/0282795 A1 | 9/2019 | Fangrow |
| 2019/0351211 A1 | 11/2019 | Dombrowski et al. |
| 2020/0139037 A1 | 5/2020 | Ziebol et al. |
| 2020/0139102 A1 | 5/2020 | Ziebol et al. |
| 2020/0139103 A1 | 5/2020 | Ziebol et al. |
| 2020/0139104 A1 | 5/2020 | Ziebol et al. |
| 2020/0324102 A1 | 10/2020 | Fangrow |
| 2020/0330741 A1 | 10/2020 | Fangrow |
| 2020/0406020 A1 | 12/2020 | Fangrow |
| 2021/0093791 A1 | 4/2021 | Anderson |
| 2021/0106805 A1 | 4/2021 | Fangrow |
| 2021/0162194 A1 | 6/2021 | Gardner |
| 2021/0205596 A1 | 7/2021 | Ziebol et al. |
| 2021/0308442 A1 | 10/2021 | Gardner |
| 2022/0226629 A1 | 7/2022 | Ziebel |
| 2022/0288258 A1 | 9/2022 | Gardner |
| 2022/0288376 A1 | 9/2022 | Ziebol |
| 2022/0313977 A1 | 10/2022 | Gugel et al. |
| 2022/0379035 A1 | 12/2022 | Anderson |
| 2022/0387685 A1 | 12/2022 | Ziebol |

(56) References Cited

U.S. PATENT DOCUMENTS

| | | |
|---|---|---|
| 2023/0069367 A1 | 3/2023 | Ziebol |
| 2023/0105566 A1 | 4/2023 | Fangrow |
| 2023/0121450 A1 | 4/2023 | Ziebol |
| 2023/0285735 A1 | 9/2023 | Ziebol |
| 2023/0288258 A1 | 9/2023 | Gardner |
| 2024/0050729 A1 | 2/2024 | Ziebol |
| 2024/0050730 A1 | 2/2024 | Fangrow |

FOREIGN PATENT DOCUMENTS

| | | |
|---|---|---|
| CA | 2 583 601 | 4/2006 |
| CA | 2825217 | 3/2007 |
| CA | 2 626 864 | 5/2007 |
| CA | 2 651 192 | 11/2007 |
| CA | 2 615 146 | 6/2008 |
| CA | 2 841 832 | 6/2019 |
| CN | 2402327 Y | 10/2000 |
| CN | 2815392 Y | 9/2006 |
| CN | 201150420 Y | 11/2008 |
| CN | 201519335 U | 7/2010 |
| CN | 106902402 | 6/2017 |
| CN | 107837428 | 3/2018 |
| DE | 3515665 | 5/1986 |
| DE | 89 06 628 U1 | 9/1989 |
| DE | 43 34 272 | 4/1995 |
| DE | 29617133 | 1/1997 |
| DE | 102007025900 | 12/2008 |
| EP | 0 063 640 | 11/1982 |
| EP | 0 088 341 | 9/1983 |
| EP | 0 108 785 | 5/1984 |
| EP | 0 174 162 | 3/1986 |
| EP | 0 227 219 | 7/1987 |
| EP | 0 237 239 | 9/1987 |
| EP | 0 245 872 | 11/1987 |
| EP | 0 257 485 | 3/1988 |
| EP | 0 639 385 | 2/1995 |
| EP | 0 734 721 | 10/1996 |
| EP | 0 769 265 | 4/1997 |
| EP | 1 061 000 | 10/2000 |
| EP | 1 331 020 | 7/2003 |
| EP | 1 471 011 | 10/2004 |
| EP | 1 442 753 | 2/2007 |
| EP | 1 813 293 | 8/2007 |
| EP | 1 977 714 | 10/2008 |
| EP | 2 444 117 | 4/2012 |
| EP | 2 606 930 | 6/2013 |
| EP | 2 671 604 | 12/2013 |
| EP | 2 731 658 | 5/2014 |
| FR | 2 493 149 A | 5/1982 |
| FR | 2 506 162 | 11/1982 |
| FR | 2 782 910 | 3/2000 |
| GB | 123221 | 2/1919 |
| GB | 2 296 182 | 6/1996 |
| GB | 2 333 097 | 7/1999 |
| GB | 2 387 772 | 10/2003 |
| JP | 57-131462 U | 8/1982 |
| JP | 04-99950 | 2/1992 |
| JP | 05-31180 A | 2/1993 |
| JP | 09-216661 A | 8/1997 |
| JP | 2000-157630 A | 6/2000 |
| JP | 2002-210011 | 7/2002 |
| JP | 2002-234567 A | 8/2002 |
| JP | 2002-291906 | 10/2002 |
| JP | 2005-218649 | 8/2005 |
| JP | 2006-182663 A | 7/2006 |
| JP | 2006-223583 A | 8/2006 |
| JP | 2009-006148 | 1/2009 |
| JP | 2011-036691 | 2/2011 |
| JP | 2011-528647 | 11/2011 |
| JP | 2012-020125 | 2/2012 |
| JP | 2013-520287 | 6/2013 |
| JP | 2014-117461 | 6/2014 |
| RU | 2 246 321 C1 | 2/2005 |
| WO | WO 1983/03975 | 11/1983 |
| WO | WO 1985/05040 | 11/1985 |
| WO | WO 93/20806 | 10/1993 |
| WO | WO 95/07691 | 3/1995 |
| WO | WO 96/35416 | 11/1996 |
| WO | WO 96/38136 | 12/1996 |
| WO | WO 1997/19701 | 6/1997 |
| WO | WO 1998/12125 | 3/1998 |
| WO | WO 1998/48872 | 11/1998 |
| WO | WO 1999/44665 | 9/1999 |
| WO | WO 2001/70199 A1 | 9/2001 |
| WO | WO 2002/05188 | 1/2002 |
| WO | WO 2002/47581 | 6/2002 |
| WO | WO 2002/49544 | 6/2002 |
| WO | WO 2003/015677 | 2/2003 |
| WO | WO 2003/070296 | 8/2003 |
| WO | WO 2004/035129 | 4/2004 |
| WO | WO 2004/112846 | 12/2004 |
| WO | WO 2005/112954 A1 | 12/2005 |
| WO | WO 2005/112974 A2 | 12/2005 |
| WO | WO 2006/007690 | 1/2006 |
| WO | WO 2006/044236 | 4/2006 |
| WO | WO 2006/102756 | 10/2006 |
| WO | WO 2007/056773 | 5/2007 |
| WO | WO 2007/137056 | 11/2007 |
| WO | WO 2008/014437 | 1/2008 |
| WO | WO 2008/042285 | 4/2008 |
| WO | WO 2008/086631 | 7/2008 |
| WO | WO 2008/089196 | 7/2008 |
| WO | WO 2008/100950 | 8/2008 |
| WO | WO 2008/140807 | 11/2008 |
| WO | WO 2009/002474 | 12/2008 |
| WO | WO 2009/060322 | 5/2009 |
| WO | WO 2009/117135 | 9/2009 |
| WO | WO 2009/123709 | 10/2009 |
| WO | WO 2009/136957 | 11/2009 |
| WO | WO 2009/153224 | 12/2009 |
| WO | WO 2010/002757 | 1/2010 |
| WO | WO 2010/002808 | 1/2010 |
| WO | WO 2010/011616 | 1/2010 |
| WO | WO 2010/034470 | 4/2010 |
| WO | WO 2010/039171 | 4/2010 |
| WO | WO 2010/062589 | 6/2010 |
| WO | WO 2011/012379 | 2/2011 |
| WO | WO 2011/028722 | 3/2011 |
| WO | WO 2011/053924 | 5/2011 |
| WO | WO 2011/106374 | 9/2011 |
| WO | WO 2011/119021 | 9/2011 |
| WO | WO 2012/118829 | 9/2012 |
| WO | WO 2012/162006 | 11/2012 |
| WO | WO 2013/009998 | 1/2013 |
| WO | WO 2013/023146 | 2/2013 |
| WO | WO 2013/082180 | 6/2013 |
| WO | WO 2012/184716 | 12/2013 |
| WO | WO 2013/192574 | 12/2013 |
| WO | WO 2014/031628 | 2/2014 |
| WO | WO 2014/074929 | 5/2014 |
| WO | WO 2014/126867 | 8/2014 |
| WO | WO 2014/140949 | 9/2014 |
| WO | WO 2014/159346 | 10/2014 |
| WO | WO 2015/119940 | 8/2015 |
| WO | WO 2015/120336 | 8/2015 |
| WO | WO 2015/164129 | 10/2015 |
| WO | WO 2015/164134 | 10/2015 |
| WO | WO 2015/168677 | 11/2015 |
| WO | WO 2015/174953 | 11/2015 |
| WO | WO 2016/182822 | 11/2016 |
| WO | WO 2017/127364 | 7/2017 |
| WO | WO 2017/127365 | 7/2017 |
| WO | WO 2018/009653 | 1/2018 |
| WO | WO 2018/071717 | 4/2018 |
| WO | WO 2018/204206 | 11/2018 |
| WO | WO 2018/237090 | 12/2018 |
| WO | WO 2018/237122 | 12/2018 |
| WO | WO 2019/178560 | 9/2019 |
| WO | WO 2019/246472 | 12/2019 |

(56) References Cited

FOREIGN PATENT DOCUMENTS

| WO | WO 2020/097366 | 5/2020 |
|---|---|---|
| WO | WO 2020/251947 | 12/2020 |
| WO | WO 2022/125474 | 6/2022 |

OTHER PUBLICATIONS

Australian Examination Report re AU Application No. 2008269133, dated Aug. 27, 2012 (4 pages).
Australian Examination Report (No. 2) re AU Application No. 2008269133, dated Jan. 9, 2013 (3 pages).
Australian Examination Report (No. 3) re AU Application No. 2008269133, dated May 1, 2013 (3 pages).
Australian Examination Report (Notice of Acceptance) re AU Application No. 2008269133, dated Nov. 14, 2013 (2 pages).
Australian Examination Report re AU Application No. 2012258435, dated Apr. 18, 2013 (4 pages).
Australian Examination Report re AU Application No. 2013100345, dated Apr. 18, 2013 (4 pages).
Australian Examination Report re AU Application No. 2013224680, dated May 19, 2015 (2 pages).
Baxter Minicap: Photographs of the Baxter Minicap (Sep. 1, 1998) (4 pages).
Baxter, "Peritoneal Dialysis Patient Connectology," Product Descriptions in 1 page, downloaded Jul. 1, 2011.
Canadian Examination Report, re CA Application No. 2,692,157, dated Apr. 27, 2011 (2 pages).
Canadian Examination Report, re CA Application No. 2,692,157, dated Jun. 6, 2011 (2 pages).
Canadian Examination Report, re CA Application No. 2,692,157, dated Jan. 23, 2013 (4 pages).
Canadian Notice of Allowance, re CA Application No. 2,692,157, dated Oct. 2, 2013 (4 pages).
Canadian Examination Report, re CA Application No. 2,846,145, dated Apr. 30, 2015 (3 pages).
Catheter Connections, "Introducing DualCap," Product Brochure in 1 page, Copyright 2011.
Charney, "Baxter Healthcare InterlinkTM IV Access System" in 1 page, from Handbook of Modern Hospital Safety. Published Mar. 1999.
Chinese Office Action, re CN Application No. 200880103854.5, dated Aug. 3, 2011 (5 pages).
Chinese Second Office Action, re CN Application No. 200880103854.5, dated Apr. 16, 2012 (4 pages).
Chinese Third Office Action, re CN Application No. 200880103854.5, dated Nov. 1, 2012 (4 pages).
Chinese Office Action, re CN Application No. 201310087320.0, dated May 4, 2014 (20 pages).
Colombian Office Action, re CO Application No. 10.000.937, dated Oct. 2012 (9 pages).
Colombian Office Action, re CO Application No. 14.094.083, dated Jul. 2015 (13 pages).
Conical Fittings: International Standard, "Conical fittings with 6% (Luer) Taper for Syringes, Needles and certain Other Medical Equipment—Part 2: Lock Fittings", Ref. No. ISO 594-2:1998. International Organization for Standardization (Sep. 1, 1998) 2nd ed. (16 pages).
Devine, redacted version of letter from David A. Divine, Esq. of Lee & Hayes, dated May 16, 2011 (3 pages).
Devine, redacted version of letter from David A. Divine, Esq. of Lee & Hayes, dated May 27, 2011 (3 pages).
Hospira, "You Work in Neverland," Lifeshield Product Brochure in 2 pages, Published 2009.
Hyprotek, "Port Protek," Product Brochure in 1 page, downloaded Sep. 19, 2011 from http://www.hyprotek.com/products.html.
ICU Medical Inc., "Oncology System Solutions," Product Brochure in 17 pages, Copyright 2013.
ICU Medical Inc., "Protective Cap," Photographs of Spiros Protective Cap in 2 pages, Product available 2013.

International Written Opinion re PCT/US08/07797, dated Sep. 11, 2008 (3 pages).
International Preliminary Report on Patentability re PCT/US08/07797, dated Dec. 22, 2009 (4 pages).
International Search Report re PCT/US2012/037772, dated Oct. 26, 2012 (5 pages).
International Written Opinion re PCT/US2012/037772, dated Oct. 26, 2012 (5 pages).
International Preliminary Report on Patentability re PCT/US2012/037772, dated Nov. 26, 2012 (7 pages).
International Search Report re PCT/US2012/038880, dated Nov. 19, 2012 (5 pages).
International Written Opinion re PCT/US2012/038880, dated Nov. 19, 2012 (8 pages).
International Preliminary Report on Patentability re PCT/US2012/038880, dated Nov. 20, 2013 (1 pages).
International Search Report re PCT/US2012/062078, dated Feb. 14, 2013 (3 pages).
International Written Opinion re PCT/US2012/062078, dated Feb. 14, 2013 (3 pages).
International Preliminary Report on Patentability re PCT/US2012/062078, dated May 6, 2014 (3 pages).
International Search Report re PCT/US2014/23140, dated Jul. 28, 2014 (3 pages).
International Written Opinion re PCT/US2014/23140, dated Jul. 28, 2014 (6 pages).
Japanese Office Action, re JP Application No. 2013-162527, dated Nov. 21, 2014 (2 pages).
Japanese Final Office Action, re JP Application No. 2010-163450, dated Apr. 3, 2015 (9 pages).
Menyhay et al., "Disinfection of Needleless Catheter Connectors and Access Ports with Alcohol May Not Prevent Microbial Entry: The Promise of a Novel Antiseptic-Barrier Cap" Infection Control Hospital and Epidemiology, vol. 27, No. 1 (Jan. 2006) (5 pages).
Mexican Office Action (Memo [2nd] concerning OA) re MX Application No. MX/a/2010/000171, Oct. 22, 2013 (1 pages).
Mexican Office Action (Memo concerning OA) re MX Application No. MX/a/2010/000171, Feb. 25, 2013 (2 pages).
New Zealand Examination Report and Notice of Acceptance, re NZ Application No. 582395, dated Jun. 13, 2011 (2 pages).
New Zealand Examination Report, re NZ Application No. 582395, dated Nov. 8, 2012 (2 pages).
New Zealand Examination Report and Notice of Acceptance, re NZ Application No. 582395, dated Dec. 5, 2012 (1 page).
New Zealand Examination Report re NZ Application No. 603404, dated Nov. 8, 2012 (2 pages).
New Zealand Examination Report (1st) re NZ Application No. 623139, dated Apr. 8, 2014 (1 pages).
New Zealand Examination Report (1st) re NZ Application No. 623141, dated Apr. 9, 2014 (1 pages).
New Zealand Examination Report (1st) re NZ Application No. 624449, dated Dec. 5, 2014 (2 pages).
Photographs of the Baxter Minicap (Sep. 1, 1998) (4 pages).
U.S. Office Action, re U.S. Appl. No. 11/821,190, dated Dec. 17, 2009 (10 pages).
U.S. Office Action, re U.S. Appl. No. 11/821,190, dated Aug. 2, 2010 (14 pages).
U.S. Interview Summary, re U.S. Appl. No. 11/821,190, dated Nov. 18, 2010 (4 pages).
U.S. Office Action, re U.S. Appl. No. 11/821,190, dated Mar. 7, 2011 (16 pages).
U.S. Office Action/Notice of Allowance, re U.S. Appl. No. 11/821,190, dated Apr. 26, 2011 (9 pages).
U.S. Notice of Allowance, re U.S. Appl. No. 11/821,190, dated Jul. 29, 2011 (6 pages).
U.S. Office Action, re U.S. Appl. No. 12/214,526, dated Jun. 9, 2011 (7 pages).
U.S. Final Office Action, re U.S. Appl. No. 12/214,526, dated Oct. 31, 2011 (8 pages).
U.S. Interview Summary, re U.S. Appl. No. 12/214,526, dated Mar. 23, 2012 (3 pages).
U.S. Office Action, re U.S. Appl. No. 13/095,516, dated Dec. 21, 2011 (27 pages).

(56) References Cited

OTHER PUBLICATIONS

U.S. Office Action/Notice of Allowance, re U.S. Appl. No. 13/095,516, dated May 16, 2012 (18 pages).
U.S. Office Action/Non-Final, re U.S. Appl. No. 13/113,777, dated Dec. 3, 2013 (13 pages).
U.S. Office Action/Final, re U.S. Appl. No. 13/113,777, dated Aug. 25, 2014 (9 pages).
U.S. Office Action/Final, re U.S. Appl. No. 13/113,777, dated Apr. 3, 2015 (9 pages).
U.S. Office Action, re U.S. Appl. No. 13/288,529, dated Apr. 8, 2015 (12 pages).
U.S. Office Action/Non-Final, re U.S. Appl. No. 13/456,853, dated Dec. 14, 2012 (16 pages).
U.S. Office Action/Final, re U.S. Appl. No. 13/456,853, dated Aug. 27, 2013 (18 pages).
U.S. Office Action, re U.S. Appl. No. 13/456,853, dated Mar. 27, 2014 (14 pages).
U.S. Office Action/Notice of Allowance, re U.S. Appl. No. 13/456,853, dated Dec. 3, 2014 (9 pages).
U.S. Office Action, re U.S. Appl. No. 13/473,057, dated Feb. 8, 2013 (20 pages).
U.S. Office Action/Final, re U.S. Appl. No. 13/473,057, dated Dec. 3, 2013 (19 pages).
U.S. Office Action, re U.S. Appl. No. 13/476,722, dated Jun. 24, 2015 (10 pages).
U.S. Office Action, re U.S. Appl. No. 13/547,650, dated Jan. 29, 2015 (9 pages).
U.S Office Action, re U.S. Appl. No. 13/560,499, dated Feb. 11, 2015 (9 pages).
U.S. Office Action, re U.S. Appl. No. 13/649,569, dated May 3, 2013 (15 pages).
U.S. Office Action/Final, re U.S. Appl. No. 13/649,569, dated Aug. 23, 2013 (19 pages).
U.S. Office Action, re U.S. Appl. No. 13/649,569, dated Apr. 14, 2014 (27 pages).
U.S. Office Action, re U.S. Appl. No. 13/649,569, dated Jan. 29, 2015 (14 pages).
U.S. Office Action, re U.S. Appl. No. 13/649,569, dated Sep. 28, 2015 (17 pages).
Antibiotic Lock Therapy Guideline, Stanford Hospital and Clinics, Pharmacy Department Policies and Procedures, issued Jun. 2011.
Otto, Mosby's Pocket Guide to Infusion Therapy. Elsevier Health Sciences, 2004. pp. 65-66. Accessed at: http://books.google.com/books?id=j8T14HwWdS4C&lpg=PP1&pg=PP1#v=onepage&f=false (Year: 2004).
Clave® Needlefree Connector, icumedical, human connections, 2 page brochure. 2012, M1-1065 Rev. 04.
Du. Y, et al. Protein adsorption on polyurethane catheters modified with a novel antithrombin-heparin covalent complex, Journal of Biomedical Materials Research Part A, 2006, 216-225.
Holmer, E. et al. The molecular-weight dependence of the rate-enhancing effect of heparin on the inhibition of thrombin, Factor Xa, Factor IXa, Factor XIa, Factor XIIa and kallikrein by antithrombin, Biochem. J. (1981) 193, 395-400.
ICU Medical Antimicrobial Microclave, first sold Jan. 21, 2010, p. 1-2.
Klement, P. et al. Chronic performance of polyurethane catheters covalently coated with ATH complex: A rabbit jugular vein model, Biomaterials, (2006), 27, 5107-5117.
Thread Check Inc., ISO 80369-7 replaces ISO 594-2:1998€, retrieved 2023; ISO 80369-7 published Oct. 2016, https://www.threadcheck.com/isl-80369/technicalinfo#gref (Year: 2016).
V-Link Luer Activated Device, with VitalShield Protective Coating, 2 page brochure, Baxter Dec. 2009.
U.S. Appl. No. 16/882,210, filed May 22, 2020.
Value Plastics, Inc., "Finger Snap Luer Lock Ring (FSLLR)," drawn by Frank Lombardi, May 29, 2011.
ICU Medical SwabPack, top-access bag of disinfecting caps for needlefree connectors, on sale at least as early as Jan. 2012.

* cited by examiner

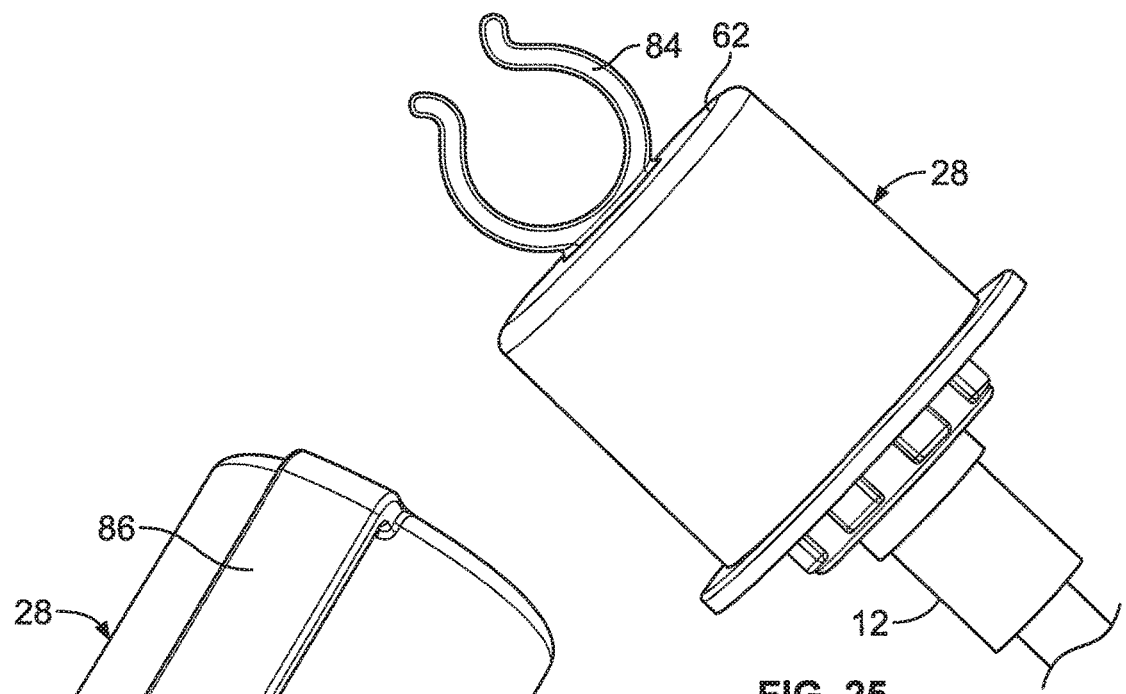
FIG. 25
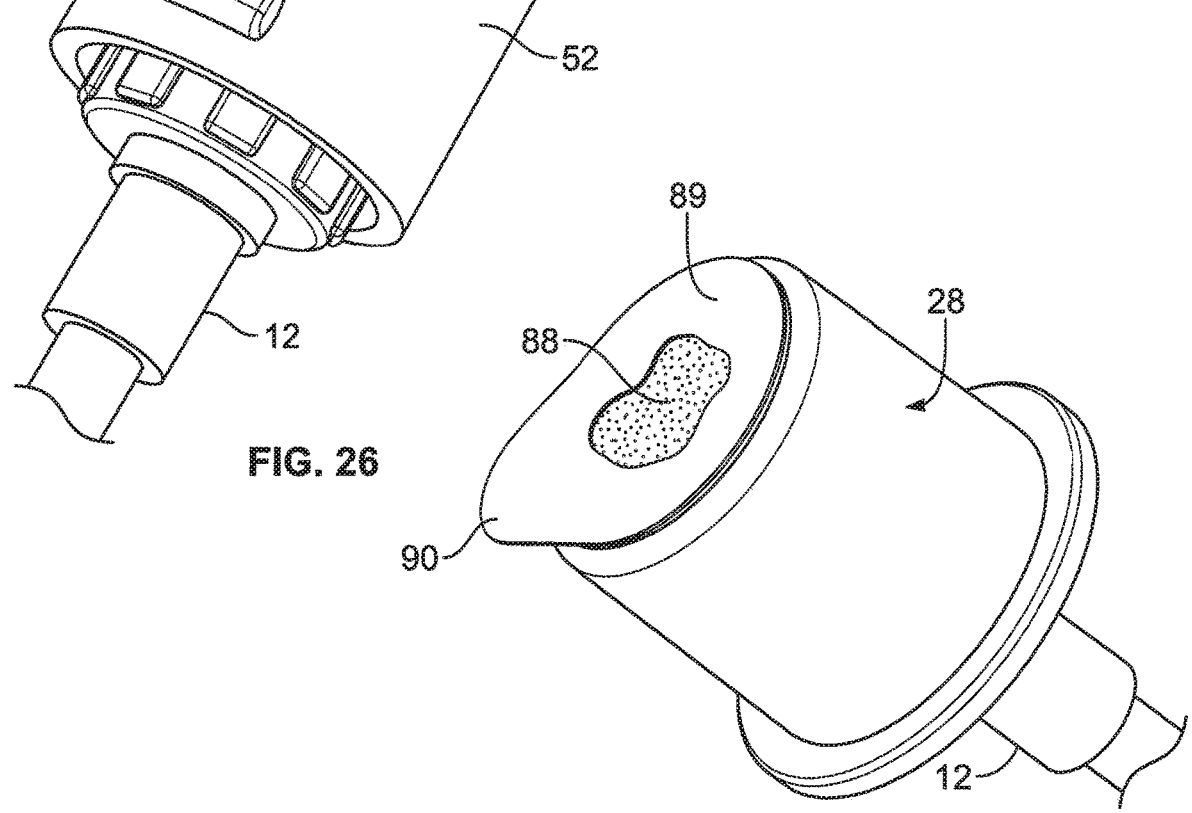
FIG. 26
FIG. 27

ANTISEPTIC CAP

CROSS-REFERENCE TO RELATED APPLICATIONS

This application is a continuation of U.S. patent application Ser. No. 16/162,106, filed Oct. 16, 2018, which is a continuation of U.S. patent application Ser. No. 13/803,289, filed on Mar. 14, 2013, now U.S. Pat. No. 10,166,381, which is a continuation-in-part of U.S. patent application Ser. No. 13/113,777, filed on May 23, 2011, now U.S. Pat. No. 9,867,975, the entire disclosure of each of which is expressly incorporated herein by reference.

BACKGROUND

Technical Field

The present invention relates to an antiseptic cap, and more particularly, to an antiseptic dead-end cap for a medical connector.

Background Art

Catheters are widely used to treat patients requiring a variety of medical procedures. Catheters can either be acute, or temporary, for short-term use or chronic for long-term treatment. Catheters are commonly introduced into central veins (such as the vena cava) from peripheral vein sites to provide access to a patient's vascular system.

In an IV dispensing system, a luer connector, e.g., a male luer connector, can have a first end and a second end. The first end of the male luer connector can be connected to a fluid line that is connected to a fluid source, such as an IV bag filled with fluid. The second end of the male luer connector can be removably attached to a first end of a female needleless luer connector. The second end of the female needleless luer connector can be attached to a catheter that has been introduced into a patient.

When the male luer connector and the female needleless luer connector are attached to each other, fluid from the IV bag can flow into the patient. These connectors are often separated from each other at various times, for example, when a patient needs to use restroom facilities. When the connectors are disengaged from each other, the connectors are exposed and are prone to contamination. Current procedures to reduce contamination of the connectors involve swabbing the connectors with a disinfection. These procedures are prone to human error and are often not implemented. Furthermore, when a male luer connector is disengaged from a female needleless connector, there is no standard manner in which to store and protect the male luer connector until it is reattached to the female connector.

SUMMARY

The present invention relates to an antiseptic dead-end cap for use with a connector that includes a base having first and second sides, a first annular wall extending from the first side of the base, a cylindrical center plug extending from the first side of the base, and a second annular wall extending from the second side of the base. The first annular wall has an outer surface and an inner surface. The cylindrical center plug has an outer surface and an inner surface, and is positioned within the first annular wall to form an annular chamber. The second annular wall has an outer surface and an inner surface, and defines a second chamber having an open end. An antiseptic material is on at least one of the inner surface of the first annular wall, the inner surface of the second annular wall, the outer surface of the second annular wall, and the outer surface of the cylindrical center plug.

The present invention further relates to an antiseptic dead-end cap for use with a connector that includes a base having first and second sides, a male connector portion extending from the first side of the base and configured to be connectable to a female luer, and a female connector portion extending from the second side of the base and configured to be connectable to a male luer. An antiseptic material is on at least a portion of the male luer connector portion or the female luer connector portion.

In some aspects, the male connector portion includes a first annular wall extending from the first side of the base and having an outer surface and an inner surface, and a cylindrical center plug extending from the first side of the base. The cylindrical center plug has an outer surface and an inner surface, and is positioned within the first annular wall to form an annular chamber. In such aspects, the female connector portion includes a second annular wall extending from the second side of the base, has an outer surface and an inner surface, and defines a second chamber having an open end.

In some aspects, the antiseptic material is a metal, while in other aspects, the antiseptic material can be an alcohol.

In other aspects, the first annular wall includes one or more threads. In still another aspect, the second annular wall includes one or more threads.

In yet another aspect, the antiseptic material is formed in at least one of the inner surface of the first annular wall, the inner surface of the second annular wall, the outer surface of the second annular wall, and the outer surface of the cylindrical center plug.

BRIEF DESCRIPTION OF THE DRAWINGS

For a more complete understanding of the present invention, reference is made to the following Detailed Description of the Invention, considered in conjunction with the accompanying drawings, in which:

FIGS. 23-27 are perspective views showing an antiseptic cap assembly with various fastening mechanisms;

DETAILED DESCRIPTION

The present invention relates to an antiseptic cap assembly that engages a male end of a luer connector. It should be understood, however, that the teachings herein can be used with other types of medical connectors.

Figure 1:
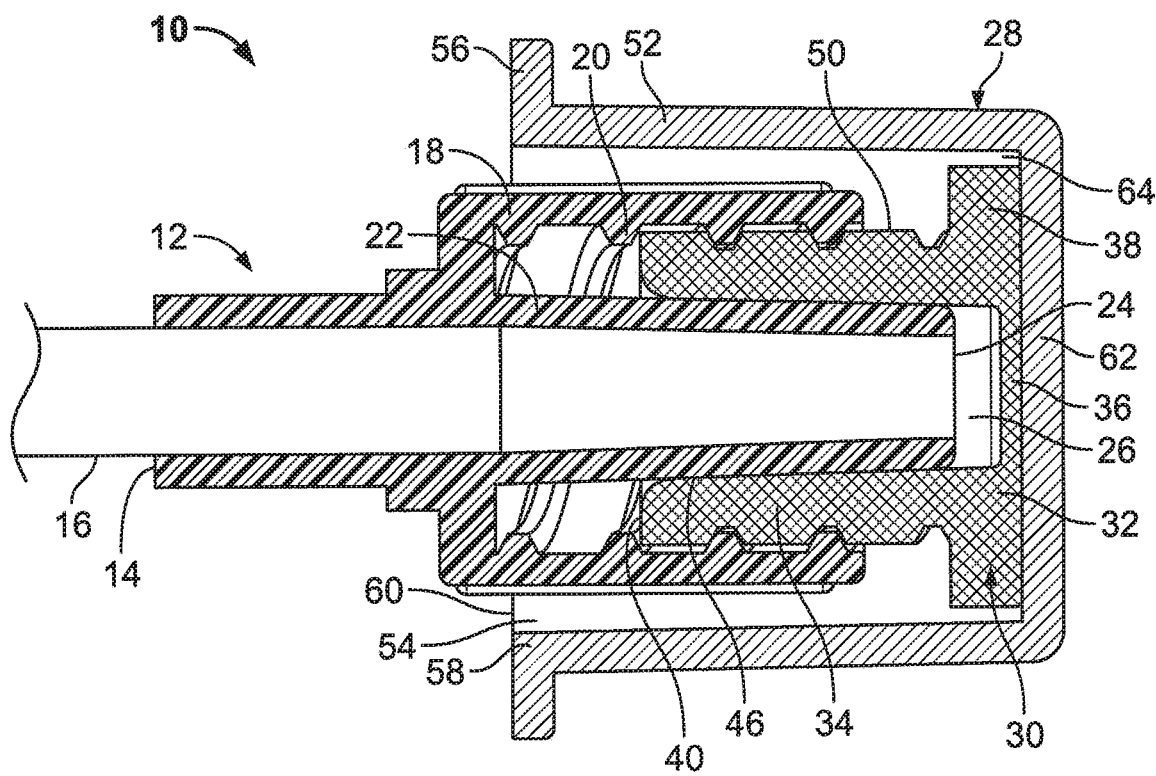
FIG. 1 is a cross-sectional view of an antiseptic cap assembly engaged to a luer connector according to the present invention.

FIG. 1 is a cross-sectional view of an antiseptic cap assembly 10 engaged to a luer connector 12. A proximal end 14 of the luer connector 12 is attached to a fluid line 16 which is connected to a fluid source (not shown), such as a IV bag filled with fluid. The luer connector 12 includes an annular threaded portion 18 with internal threads 20 and a frustoconical male luer 22 positioned for insertion into a female luer connector (not shown). The male luer 22 includes a tip 26 having an opening 24 in fluid communication with the fluid line 16. The male luer 22 is arranged substantially concentrically within the threaded portion 18. As a result of their generally coaxial arrangement, the male luer 22 and the threaded portion 18 cooperate to form an annular space therebetween.

The antiseptic cap assembly 10 includes a cap holder 28 and a cap 30 sized to be positioned within the cap holder 28. The cap 30 includes a base 32 and an annular threaded portion 34 extending from the base 32. The base 32 could include a substantially flat surface 36 and an outer flange 38.

Figure 3:
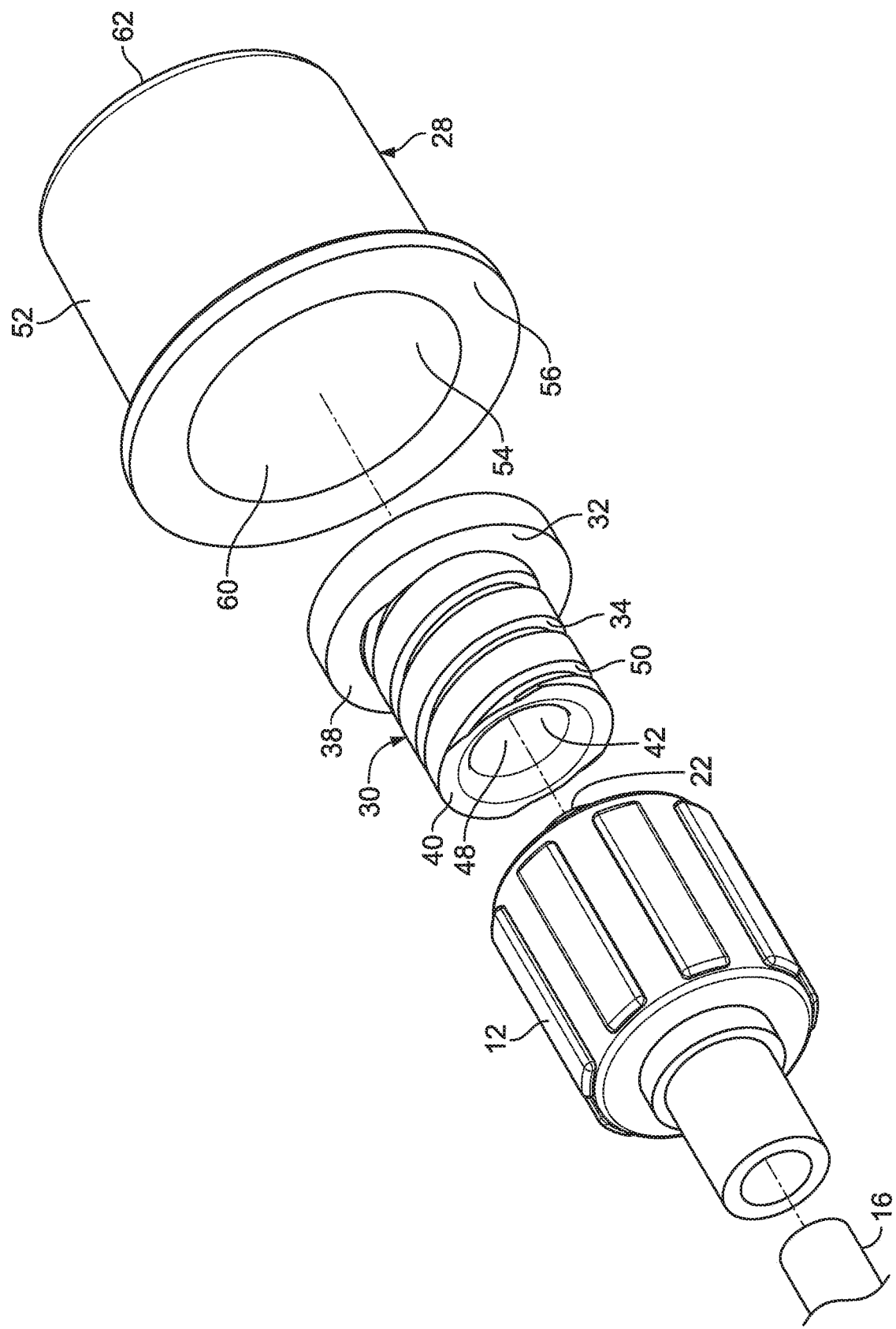
FIG. 3 is an exploded perspective view showing the antiseptic cap assembly of FIG. 1 and a luer connector.

The threaded portion 34 of the cap 30 includes a rim 40 that defines an open end 42 (see FIG. 3). The base 32 closes the opposite end of the threaded portion 34. The threaded portion 34 could be formed with a tapered inner surface 46 that compliments the male luer 22 of the luer connector 12. In particular, the tapered inner surface 46 narrows from the rim 40 toward the base 32. The threaded portion 34 defines a chamber 48 (see FIG. 3) sized to receive the male luer 22. The threaded portion 34 includes external threads 50 for engaging the threads 20 of the luer connector 12. The external threads 50 and the threads 20 of the luer connector 12 cooperate with each other so as to allow the cap 30 to be securely threadedly connected to the luer connector 12 and also to allow relative movement between the cap 30 and the luer connector 12, as the cap 30 is rotated relative to the luer connector 12. The external threads 50 extend between the base 32 and the rim 40.

The configuration of the cap 30 is shown in perspective in FIG. 3. It should be noted that this configuration is exemplary. For example, the cap 30 could be configured without threads and sized to engage the luer connector 12 with a push-on friction fit, as will be described hereinafter.

The cap 30 could be made from an absorbent material. The cap 30 could be made from porous plastic, for example, a medical grade sintered porous plastic material which is available from Porex Corporation, based in Fairburn, GA Other suitable manufacturers of the porous plastic material include Filtrona, Genpore, and Thermopore. It is desirable that the material can absorb and retain a fluid such as an antiseptic fluid. It is also desirable that the material is sufficiently rigid to maintain its structure. It is also desirable that the material is compressible and that the absorbed fluid is released on compression. The porous plastic material could be made of any suitable polymer, such as polyethylene, polypropylene, nylon, etc.

The use of the porous plastic material is only exemplary. It will be understood that the cap 30 could be made from any other suitable material, such as bonded fiber, cotton, silicone, urethane, polyester, cellulose, etc. The material could be natural or synthetic.

The threaded portion 34 of the cap 30 could be coated or impregnated with an antiseptic fluid, an anticoagulant fluid, and/or an antimicrobial fluid. An example of a suitable antiseptic fluid is isopropyl alcohol. The concentration of the isopropyl alcohol could vary, and is preferably 70% v/v. The concentration of alcohol could be in a range from 20% to 100%. It will be understand that other materials could be used, such as other alcohols, including ethanol, propanol, and/or butanol, or iodine, hydrogen peroxide, chlorhexidine gluconate, chlorhexidine acetate, etc. The antiseptic, anticoagulant, and/or antimicrobial agent could be in liquid or solid form.

The cap holder 28 includes a cylindrically shaped sidewall 52 that defines a chamber 54 sized to receive the cap 30 and accommodate the male luer 22. The cap holder 28 could include an outer flange 56 that protrudes radially outwardly from a distal end 58 of the sidewall 52. The outer flange 56 defines an open end 60. The cap holder 28 could include a substantially flat surface 62 that defines the opposite, closed end. The cap holder 28 could be made from a thermoplastic elastomer, such as the thermoplastic elastomer sold by ExxonMobil under the trademark SANTOPRENE, or any other suitable material. The cap holder 28 could be made from a more rigid material, such as a high-density polyethylene. The cap holder 28 and the cap 30 could be bonded to each other, or attached to each other by any suitable method, such as by adhesive or by molding.

When the cap 30 is attached to the cap holder 28, a gap 64 may exist between the flange 38 of the cap 30 and the cap holder 28, and between the threaded portion 34 of the cap 30 and the cap holder 28. Also, the cap 30 is attached to the cap holder 28 such that the cap 30 rotates conjointly with the cap holder 28.

Figure 2:
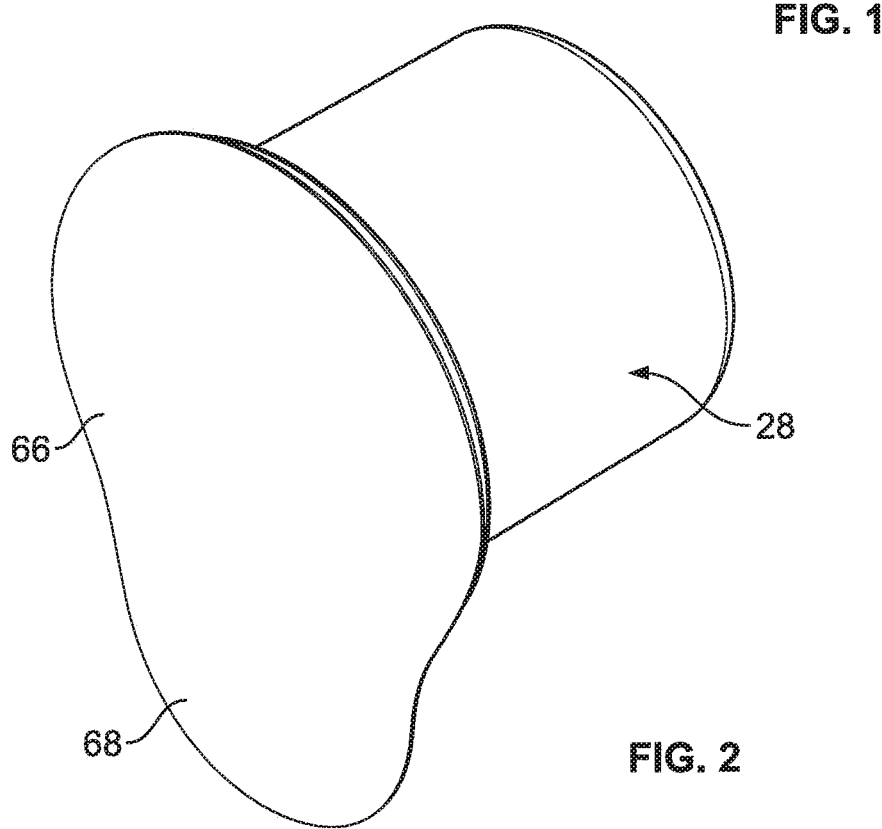
FIG. 2 is a perspective view of a sealed antiseptic cap assembly.

As shown in FIG. 2, the cap holder 28 could be sealed with a material, such as a film 66, a foil material or lid stock material, which can be attached to the flange 56 by any suitable method such as by adhesive or by conductive or inductive heat sealing techniques. A pull tab 68 could be provided to facilitate removal of the film 66 to provide access to the antiseptic cap 10.

Generally, the cap 30 may be hydrophobic. However, because the hydrophobic material could serve to inhibit or minimize an antiseptic fluid, such as isopropyl alcohol, from passing through the cap 30, it may be desirable to make at least a portion of the cap 30 hydrophilic. For example, it may be desirable to treat at least a portion of the cap 30 with a hydrophilic surfactant. In this manner, the hydrophilic portion could allow the alcohol to pass therethrough, whereas the hydrophobic portion could serve to inhibit or minimize an antiseptic fluid, such as isopropyl alcohol, from passing therethrough. In one embodiment, the threaded portion 34 could be treated with a hydrophilic surfactant whereas the base 32 could remain hydrophobic, so as to be resistant to an antiseptic fluid, such as alcohol. The hydrophobic section could also act as a plug to prevent IV fluid from leaking through the tubing to go past the cap 30.

Figure 4:
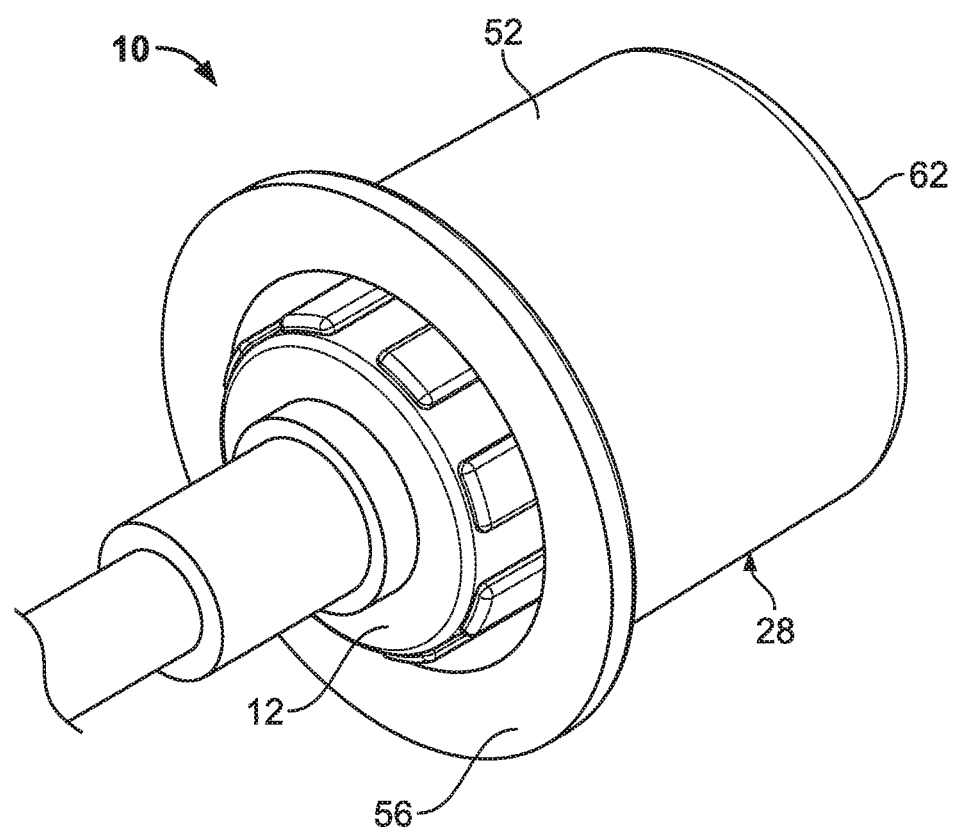
FIG. 4 is a perspective view of the antiseptic cap assembly of FIG. 1 engaged to a luer connector.

Referring to FIG. 1, the antiseptic cap assembly 10 is shown attached to the luer connector 12 such that the threaded portion 34 of the cap 30 mates with the threads 20 of the luer connector 12 and the base 32 is positioned adjacent the opening 24 of the male luer 22. Also, in this position, the inner surface 46 of the threaded portion 34 is adjacent the male luer 22 and the male luer 22 compresses the cap 30 to release at least a portion of the antiseptic fluid to disinfect the luer connector 12. The antiseptic cap assembly 10 can be allowed to remain attached to the luer connector 12 for any suitable period of time. When the antiseptic cap assembly 10 is attached to the luer connector 12, as shown in the perspective view of FIG. 4, the luer connector 12 is exposed to the antiseptic fluid.

The cap holder 28 could be configured to remain on the cap 30 after the antiseptic cap assembly 10 engages the luer connector 12. Alternatively, the cap holder 28 could be configured to be removably attached to the cap 30. For example, the cap holder 28 could be removed from the cap 30 after the antiseptic cap assembly 10 engages the luer connector 12.

Figure 5:
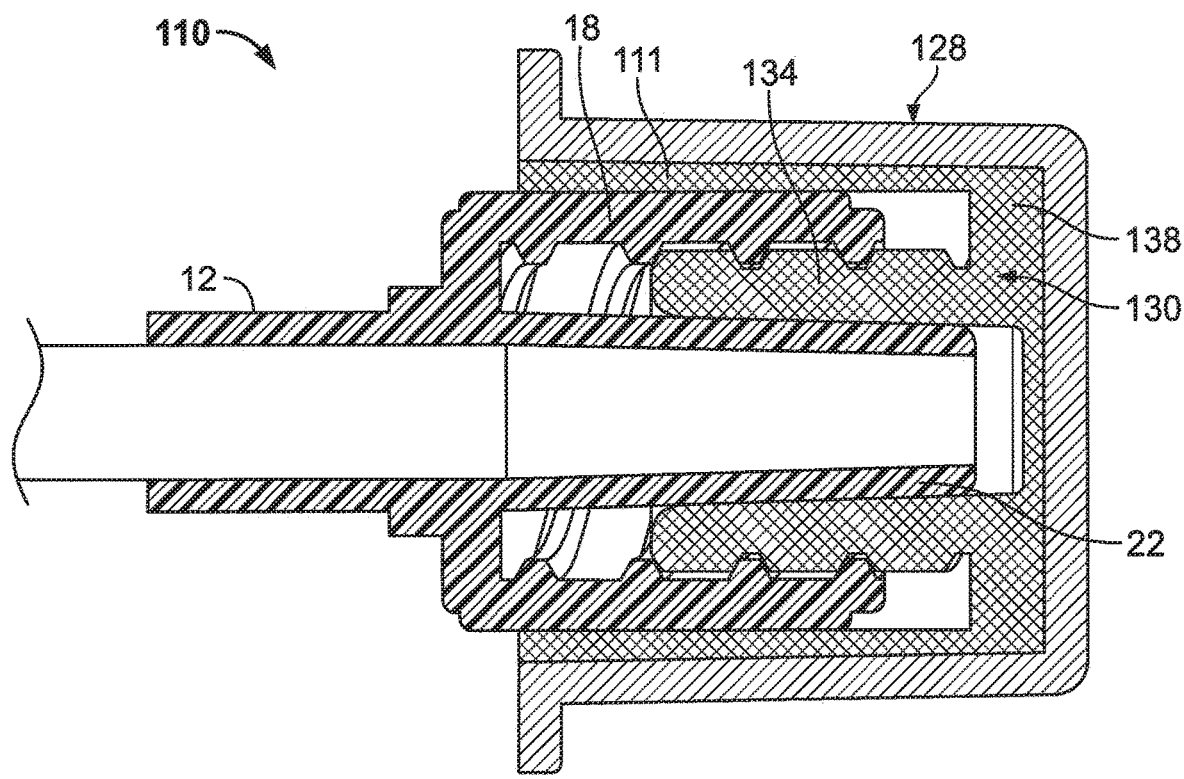
FIG. 5 is a cross-sectional view showing an antiseptic cap assembly, wherein a cap has an outer wall.

FIG. 5 shows an antiseptic cap assembly, indicated generally as 110, that is sized to engage and disinfect the male luer 22. The antiseptic cap assembly 110 operates and is constructed in manners consistent with the antiseptic cap assembly 10 shown in FIGS. 1-4, unless stated otherwise. Like the antiseptic cap assembly 10, the antiseptic cap assembly 110 includes a cap holder 128 and a cap 130 sized to be positioned within the cap holder 128.

Cap 130 includes an annular sidewall 111 extending from an outer flange 138 and substantially concentric with the threaded portion 134. When the cap holder 128 is used, the annular sidewall 111 is positioned proximate an outer surface of the cap holder 12. When the antiseptic cap assembly 110 is attached to the luer connector 12, the annular sidewall 111 bears against the outer surface of the threaded portion 18 of the luer connector 12. The annular sidewall 111 can be made from porous plastic like the remainder of the cap 130 or any other suitable material. The annular sidewall 111 covers and protects the outer surface of the threaded portion 18 of the luer connector 12. The annular sidewall 111 may contain antiseptic fluid and release at least a portion of an antiseptic fluid.

Figure 6:
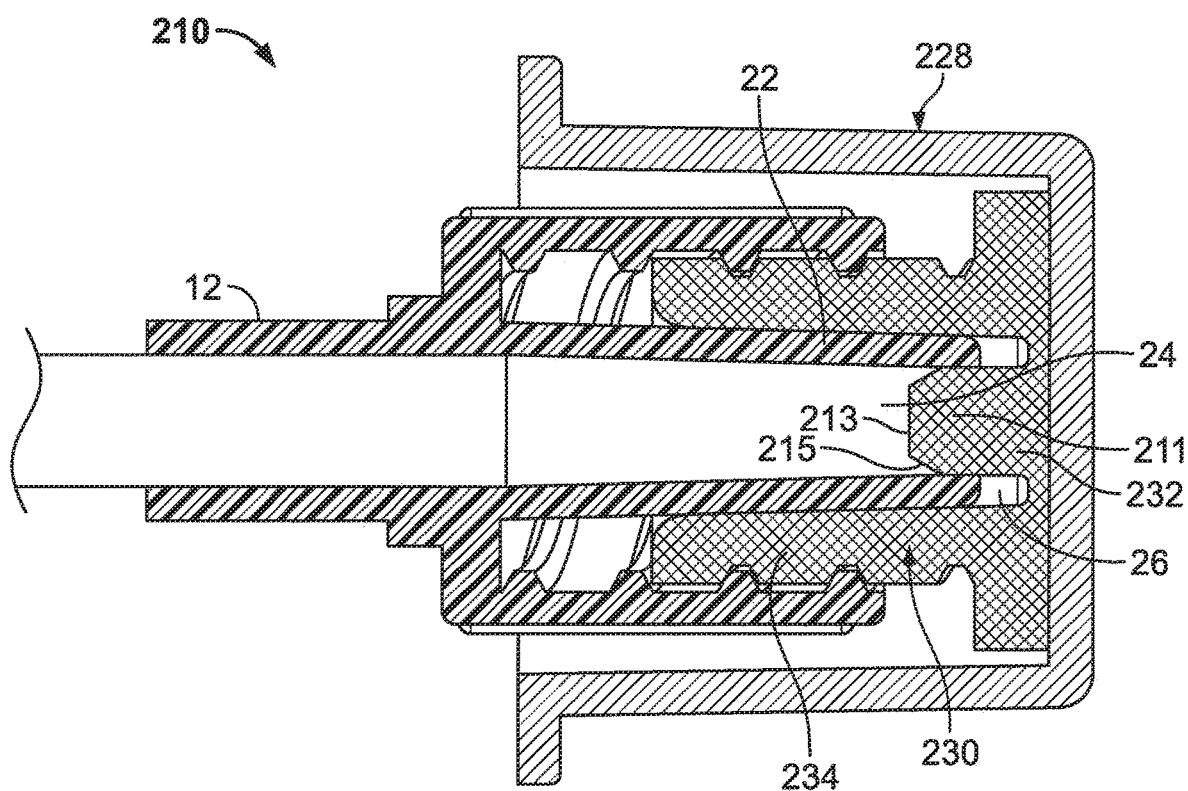
FIG. 6 is a cross-sectional view showing an antiseptic cap assembly, wherein the cap includes a center insert.

FIG. 6 shows an antiseptic cap assembly, indicated generally as 210, that is sized to engage and disinfect a male luer 22. The antiseptic cap assembly 210 operates and is constructed in manners consistent with the antiseptic cap assembly 10 shown in FIGS. 1-4, unless stated otherwise. Like the antiseptic cap assembly 10, the antiseptic cap assembly 210 includes a cap holder 228 and a cap 230 sized to be positioned within the cap holder 228.

Cap 230 includes a center insert 211 that is integrally connected therewith. Alternatively, the cap 230 and the center insert 211 could be separate components. The center insert 211 may be made from porous plastic like the remainder of the cap 230 or any other suitable material, and may contain antiseptic fluid and release at least a portion of an antiseptic fluid. The center insert 211 could be treated with a hydrophilic surfactant, or otherwise made hydrophilic.

The center insert 211 protrudes from a base 232 of the cap 230 and is positioned within a threaded portion 234 of the cap 230. The center insert 211 has a distal end 213 that may have angled edges 215, thereby giving the center insert 211 a generally trapezoidal shape. The center insert 211 could define other shapes such as conical, square, rectangle, etc.

When the cap 230 is attached to a luer connector 12, the center insert 211 is positioned within the opening 24 formed in the male luer 22 and allows the antiseptic fluid to enter the male luer 22 to apply the antiseptic fluid to the inner tip 26 of the male luer 22.

Figure 7:
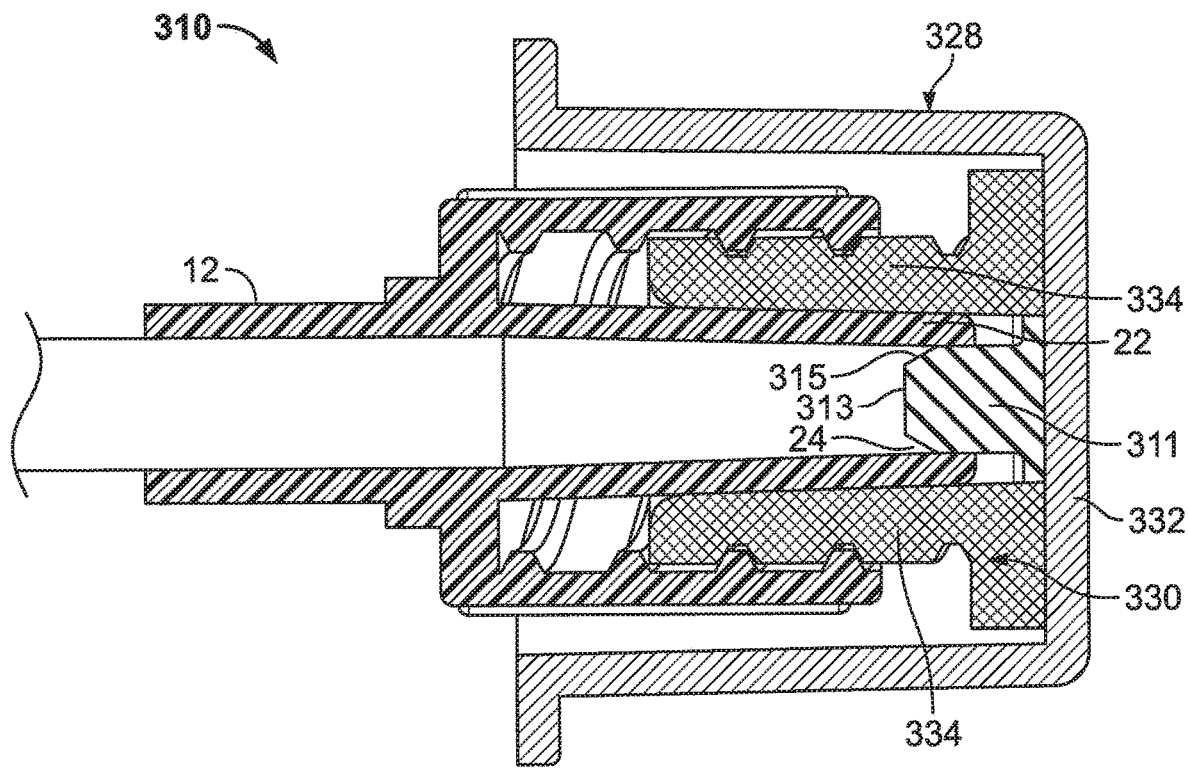
FIG. 7 is a cross-sectional view showing an antiseptic cap assembly, wherein the cap includes a center plug.

FIG. 7 shows an antiseptic cap assembly, indicated generally as 310, that is sized to engage and disinfect a male luer 22. The antiseptic cap assembly 310 operates and is constructed in manners consistent with the antiseptic cap assembly 10 shown in FIGS. 1-3, unless stated otherwise. Like the antiseptic cap assembly 10, the antiseptic cap assembly 310 includes a cap holder 328 and a cap 330 sized to be positioned within the cap holder 328.

A sealing mechanism, such as a center plug 311, is sized to extend from a base 332 of the cap 330 and is sized to be positioned within the threaded portion 334 of the cap 330. The cap 330 and the center plug 311 could be separate components as shown or, alternatively, the cap 330 and the center plug 311 could be integrally formed. Alternatively, the center plug 311 could be an extension of the cap holder 328 molded in.

The center plug 311 has a distal end 313 that may have angled edges 315, thereby giving the center plug 311 a generally trapezoidal shape. The center plug 311 could define other shapes such as conical, square, rectangle, etc.

The center plug 311 bears against the opening 24 formed in the male luer 22 to prevent the antiseptic fluid from entering the male luer 22. The center plug 311 extends a distance from the base 332 sufficient to engage the opening 24 in the male luer 22 before the threaded portion 334 of the cap 330 is compressed by the male luer 22, to seal the opening 24 in the male luer 22.

The center plug 311 could be made of a non-porous material, such as rubber, or any other suitable material. The center plug 311 could be made of porous plastic and left in a hydrophobic state, i.e., not treated with a surfactant like the threaded portion 334 of the cap 330, thereby inhibiting or minimizing antiseptic fluid from passing therethrough and into the opening 24 formed in the male luer 22. In this manner, the center plug 311 serves to limit or prevent alcohol from entering the fluid line 316 of the luer connector 312. Also the center plug 311 could act as a plug to prevent IV fluid from dripping out of the line.

The configuration of the sealing mechanism is only exemplary. It will be understood that the present invention could employ other sealing mechanisms. For example, the sealing mechanism could be a center pin (not shown) sized to extend further into the opening 24 formed in the male luer 22 than the center plug 311. The center plug 311 may extend past the threads on the threaded portion 324 and inserted prior to thread engagement.

Figure 8:
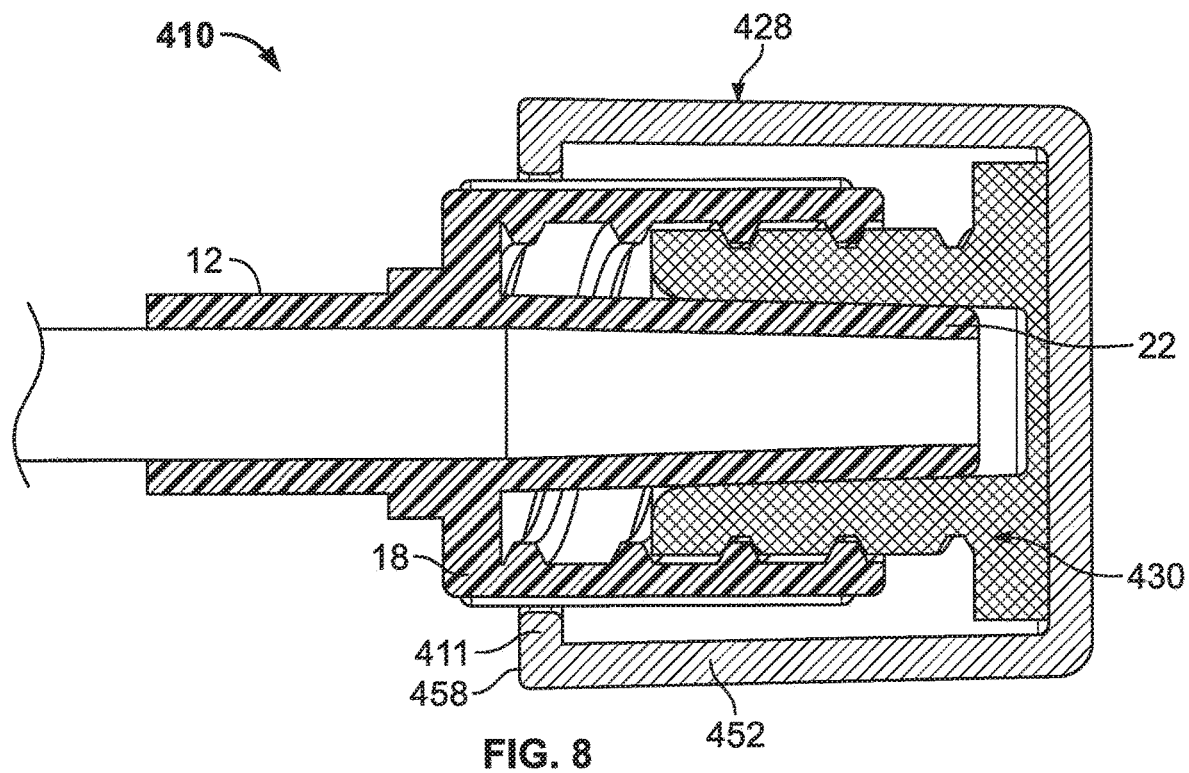
FIG. 8 is a cross-sectional view showing an antiseptic cap assembly, wherein a cap holder includes an inner-facing flange.

FIG. 8 shows an antiseptic cap assembly, indicated generally as 410, that is sized to engage and disinfect a male luer 22. The antiseptic cap assembly 410 operates and is constructed in manners consistent with the antiseptic cap assembly 10 shown in FIGS. 1-4, unless stated otherwise. Like the antiseptic cap assembly 10, the antiseptic cap assembly 410 includes a cap holder 428 and a cap 430 sized to be positioned within the cap holder 428.

The cap holder 428 includes an inner-facing flange 411 that may form a protective seal that closes off the interior of the cap holder 428 when the antiseptic cap assembly 410 is engaged to the luer connector 12. The inner flange 411 extends radially inward from a distal end 458 of the sidewall 452 of the cap holder 428. When the antiseptic cap assembly 410 is engaged to the luer connector 12, the inner-facing flange 411 of the cap holder 428 may contact the threaded portion 18 of the luer connector 12 to seal the interior of the cap holder 428.

The inner-facing flange 411 of the cap holder 428 may provide a physical barrier to the ingress of pathogens, dust or other contaminants into the cap holder 428. The inner-facing flange 411 may serve to retain at least a portion of the antiseptic fluid from the antiseptic cap assembly 410 from leaking out. The inner-facing flange 411 may prevent evaporation of at least a portion of the antiseptic fluid that is retained.

The configuration of the cap holder 428 could vary. For example, the cap holder 428 could include an outer flange (not shown), such as the outer flange 56 (FIG. 1) that protrudes radially outwardly from the distal end 458 of the sidewall 452, as well as the inner-facing flange 411 that protrudes radially inward from the distal end 458 of the sidewall 452.

Figure 9:
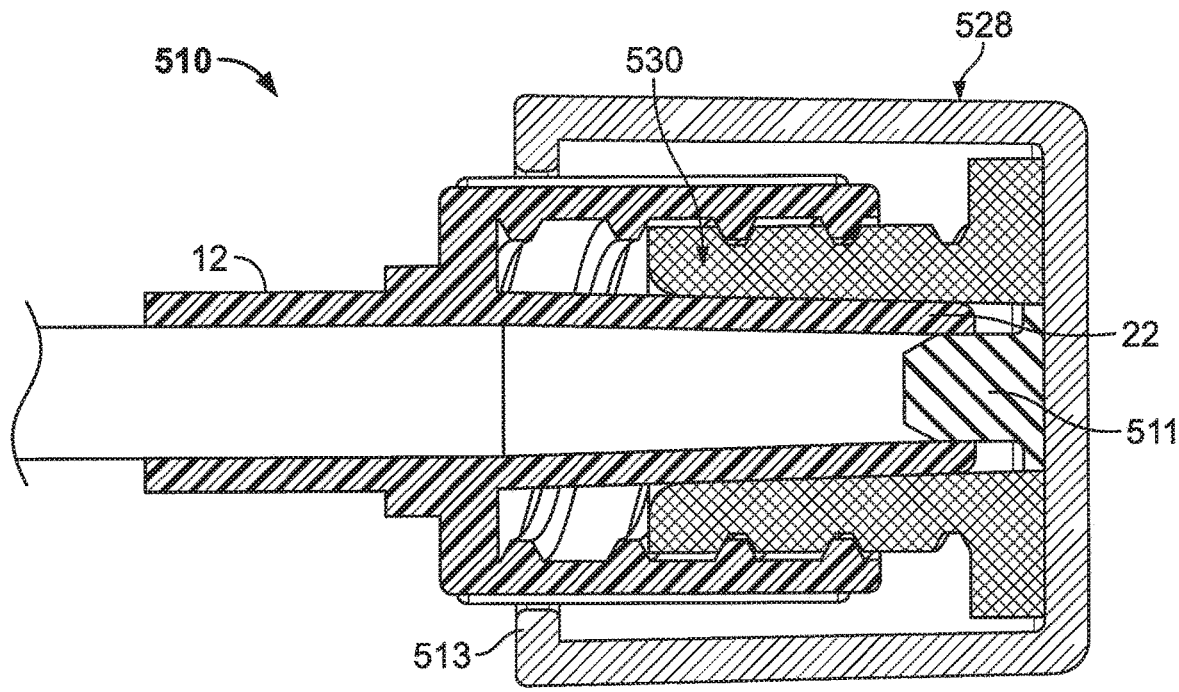
FIG. 9 is a cross-sectional view showing an antiseptic cap assembly, wherein a center plug is provided and the cap holder includes an inner-facing flange.

FIG. 9 shows an antiseptic cap assembly, indicated generally as 510, that is sized to engage and disinfect a male luer 22. The antiseptic cap assembly 510 operates and is constructed in manners consistent with the antiseptic cap assembly 10 shown in FIGS. 1-4, unless stated otherwise. Like the antiseptic cap assembly 10, the antiseptic cap assembly 510 includes a cap holder 528 and a cap 530 sized to be positioned within the cap holder 528.

The antiseptic cap assembly 510 includes a center plug 511, such as the center plug 311 shown in FIG. 7. In addition, the cap holder includes an inner-facing flange 513, such as the flange 411 shown in FIG. 8.

It should be understood that various features of various embodiments disclosed herein could be used together without departing from the spirit or scope of the present invention.

Figure 10:
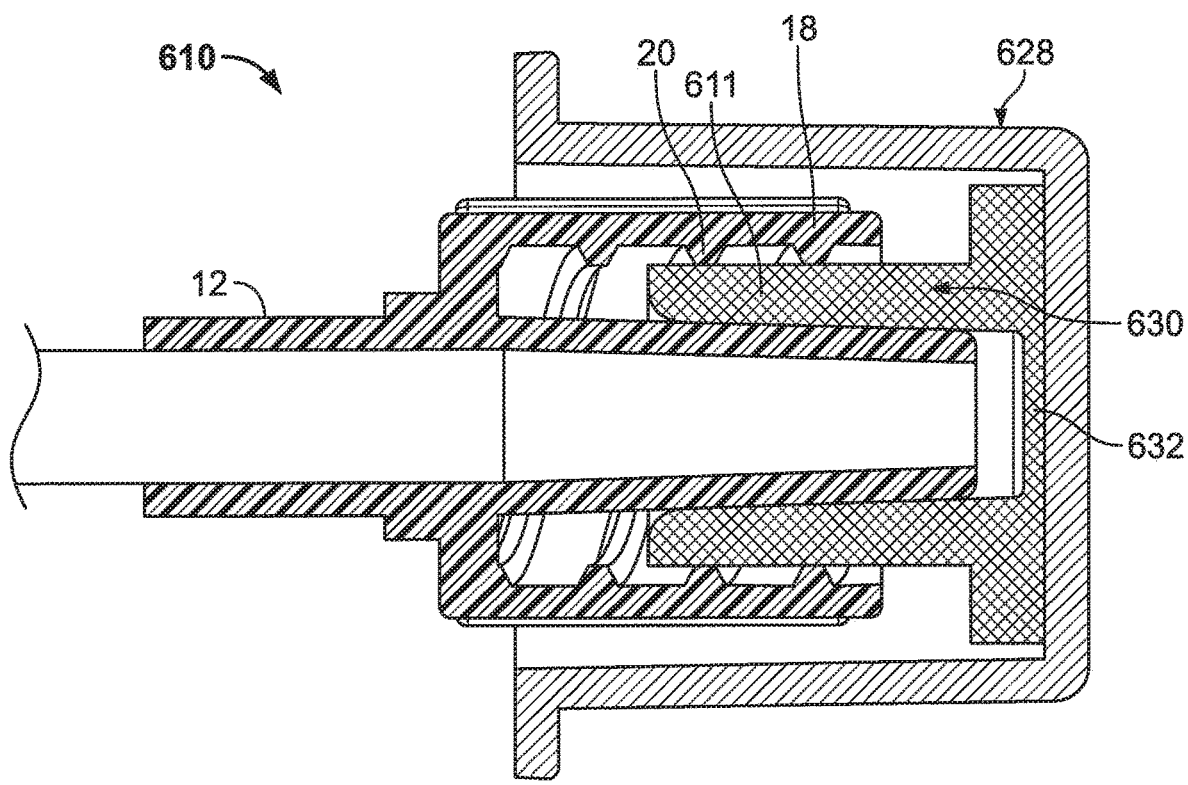
FIG. 10 is a cross-sectional view showing an antiseptic cap assembly, wherein a cap includes an annular portion without threads.

FIG. 10 shows an antiseptic cap assembly, indicated generally as 610, that is sized to engage and disinfect a male luer 22. The antiseptic cap assembly 610 operates and is constructed in manners consistent with the antiseptic cap assembly 10 shown in FIGS. 1-4, unless stated otherwise. Like the antiseptic cap assembly 10, the antiseptic cap assembly 610 includes a cap holder 628 and a cap 630 sized to be positioned within the cap holder 628.

The cap 630 includes an annular portion 611 extending from a base 632. The annular portion 611 is configured without threads but is sized to engage the luer connector 12 with a push-on friction fit. The antiseptic cap assembly 610 could be removed by pulling out of the luer connector 12.

The annular portion 611 of the cap 630 could be configured such that the inner surface contacts the male luer 22 and is compressed by the male luer 22 to release antiseptic fluid when the cap 630 is pushed on to the male luer 22. The outer surface of the annular portion 611 could also contact against the inner threads 18 of the threaded portion 18 of the male luer 22 and could also release antiseptic fluid on this side. Alternatively, the annular portion 611 could be configured to avoid contact with the threads 20 of the luer connector 12. The annular portion 611 does not need to be tapered as shown.

Figure 11:
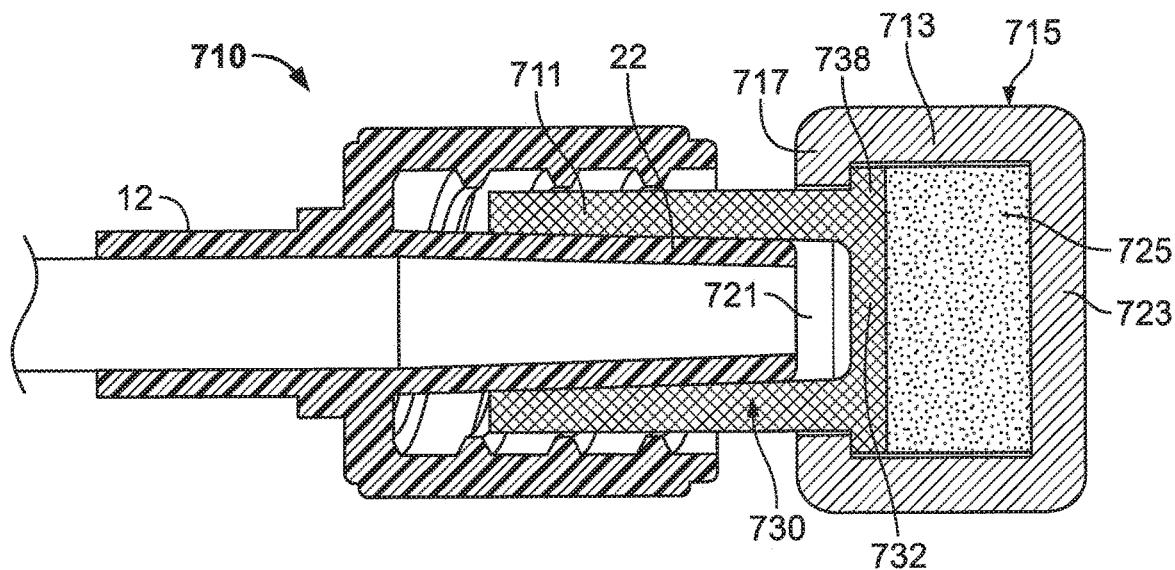
FIG. 11 is a cross-sectional view showing an antiseptic cap assembly that includes an antiseptic chamber.
Figure 12:
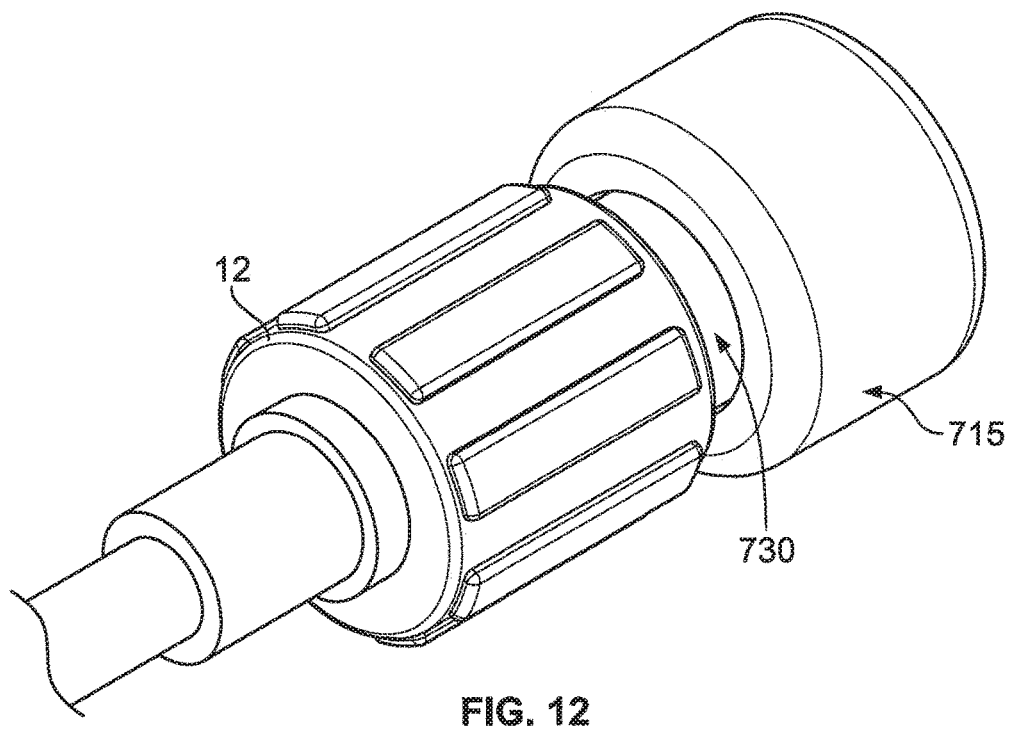
FIG. 12 is a perspective view of the antiseptic cap assembly shown in FIG. 11.

FIGS. 11 and 12 show an antiseptic cap assembly, indicated generally as 710, that is sized to engage and disinfect a male luer 22. The antiseptic cap assembly 710 operates and is constructed in manners consistent with the antiseptic cap assembly 10 shown in FIGS. 1-3, unless stated otherwise. The antiseptic cap assembly 710 includes an antiseptic chamber 715 and a cap 730.

The cap 730 includes an annular portion 711 extending from a base 732. The annular portion 711 is configured and sized to engage the luer connector 12 with a push-on friction fit.

The antiseptic chamber 715 is attached to the base 732 of the cap 730 and is formed by a continuous sidewall 713 and an end wall 723. The sidewall 713 includes an inner flange 717 that extends radially inward from the sidewall 713. The flange 717 defines an open end 721.

The base 732 of the cap 730 is keyed to the antiseptic chamber 715. The base 732 of the cap 730 is positioned within the antiseptic chamber 715 such that the outer flange 738 of the base 732 is captured in the antiseptic chamber 715 by the inner flange 717 of the antiseptic chamber 715 which extends over the base 732. The base 732 closes off the disinfectant chamber 715 and the annular portion 711 of the cap 730 is in contact with the inner flange 717 of the antiseptic chamber 715. The cap 730 could be attached to the antiseptic chamber 715 such that the cap 730 rotates conjointly with the antiseptic chamber 715. In one embodiment, the base 732 of the cap 730 does not need to be keyed to the antiseptic chamber 715 in a push-on design.

The antiseptic chamber 715 can include an absorbent material 725, such as a pad, sponge, or elastomeric foam, configured to retain an antiseptic fluid. The absorbent material 725 could be wetted or soaked with the antiseptic fluid. The absorbent material 725 could be deformable. The cap 730 could be made from a porous plastic material that serves as a carrier for the transfer of antiseptic fluid from the disinfectant chamber 715. When the cap holder 728 is compressed, the absorbent material 725 releases at least a portion of the antiseptic fluid. The fluid can then flow through the base 732 and along the annular portion 711 to be delivered to the male luer 22. FIG. 12 shows a perspective view of the antiseptic cap assembly 710.

It will be understood that the present invention could employ other mechanisms that involve pushing on a component of an antiseptic cap assembly to activate or release the antiseptic fluid.

Figure 13:
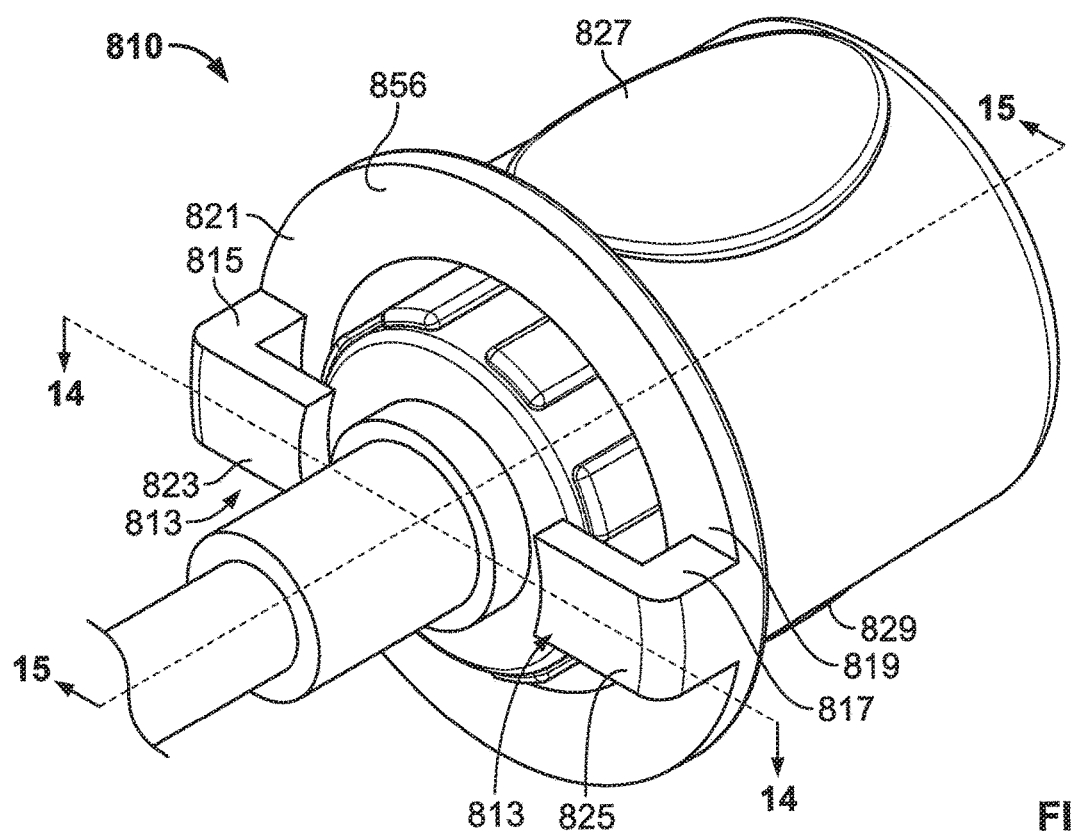
FIG. 13 is a perspective view showing an antiseptic cap assembly, wherein a cap holder includes retainers.
Figure 14:
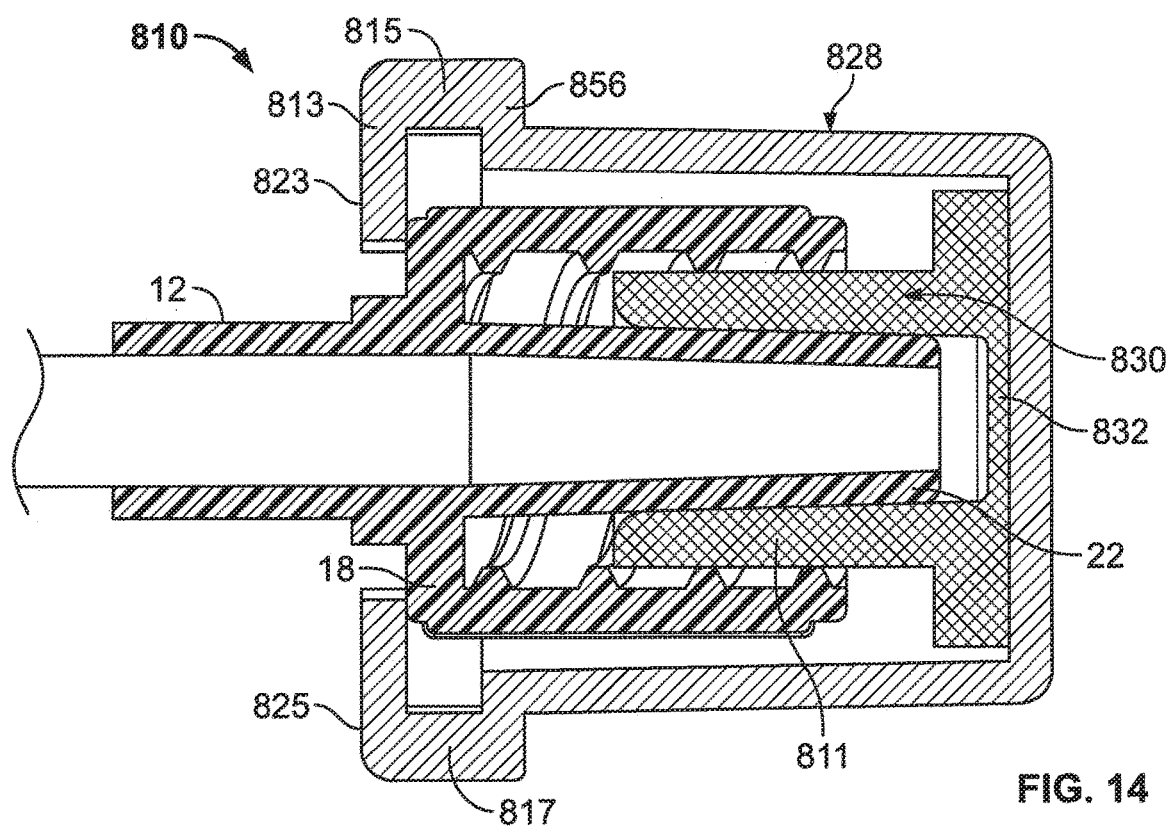
FIG. 14 is a cross-sectional view, taken along section lines 14-14 and looking in the direction of the arrows, of the antiseptic cap assembly shown in FIG. 13.
Figure 15:
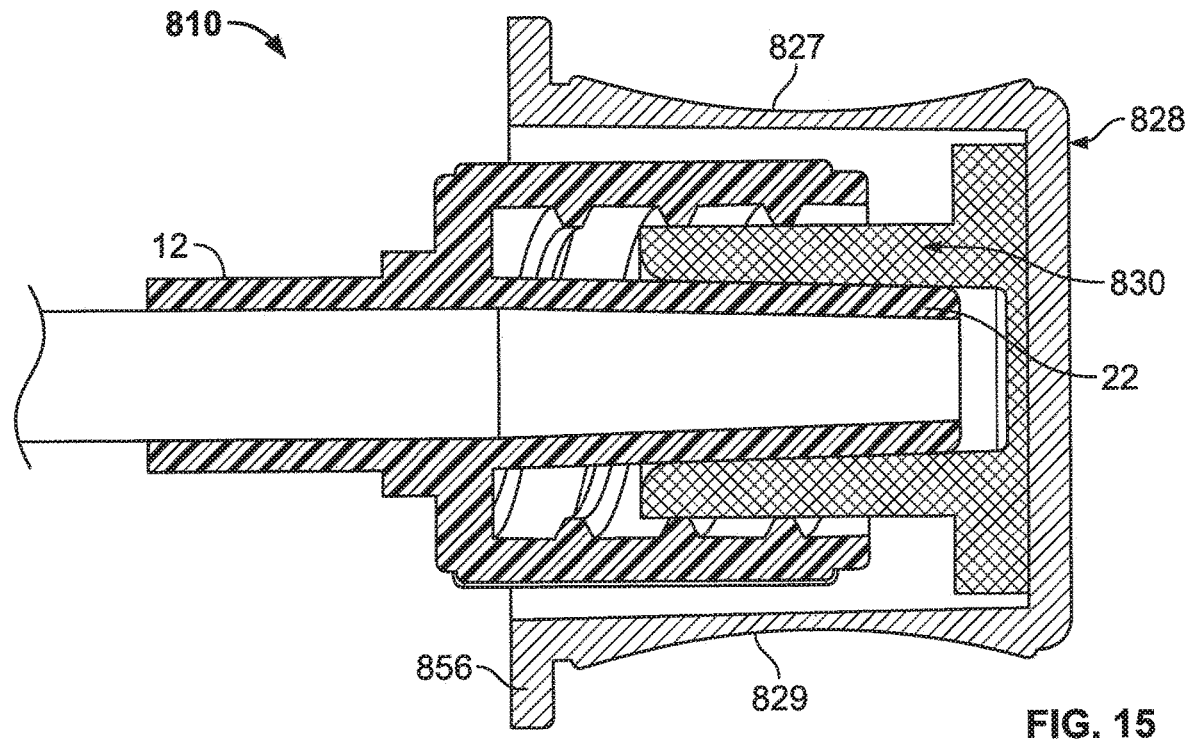
FIG. 15 is a cross-sectional view, taken along section lines 15-15, of the antiseptic cap assembly shown in FIG. 13.

FIGS. 13-15 show an antiseptic cap assembly, indicated generally as 810, that is sized to engage and disinfect a male luer 22. The antiseptic cap assembly 810 operates and is constructed in manners consistent with the antiseptic cap assembly 10 shown in FIGS. 1-3, unless stated otherwise.

Like the antiseptic cap assembly 10, the antiseptic cap assembly 810 includes a cap holder 828 and a cap 830 sized to be positioned within the cap holder 828.

The cap 830 includes an annular portion 811 extending from a base 832. The annular portion 811 is configured without threads and sized to engage the luer connector 12 with a push-on friction fit. The antiseptic cap assembly 810 could be removed by pulling out of the luer connector 12.

The cap holder 828 includes retainers 813 that serve to retain or secure the cap 830 on the luer connector 12. The retainers 813 include a pair of shoulders 815, 817 that extend perpendicularly from opposite sides of the outer flange 856 of the cap holder 828 and a pair of arms 823, 825 that extend radially inward from the shoulders 815, 817.

When the antiseptic cap assembly 810 is engaged to the luer connector 12, the arms 823, 825 of the retainers 813 extend over the male luer 22 to retain the cap 830. The retainers 813 could be made from a thermoplastic elastomer, such as SANTOPRENE, or any other suitable material. The retainers 813 could be made from a flexible material.

The cap holder 828 may include gripping areas defined by a recessed portion 827 (FIGS. 13 and 15) and a recessed portion 829 (FIGS. 13 and 15) on opposite sides of the outer sidewall 852. The recessed portions 827, 829 are configured for gripping the cap 830 to attach the cap 830 to the male luer 22.

Figure 16:
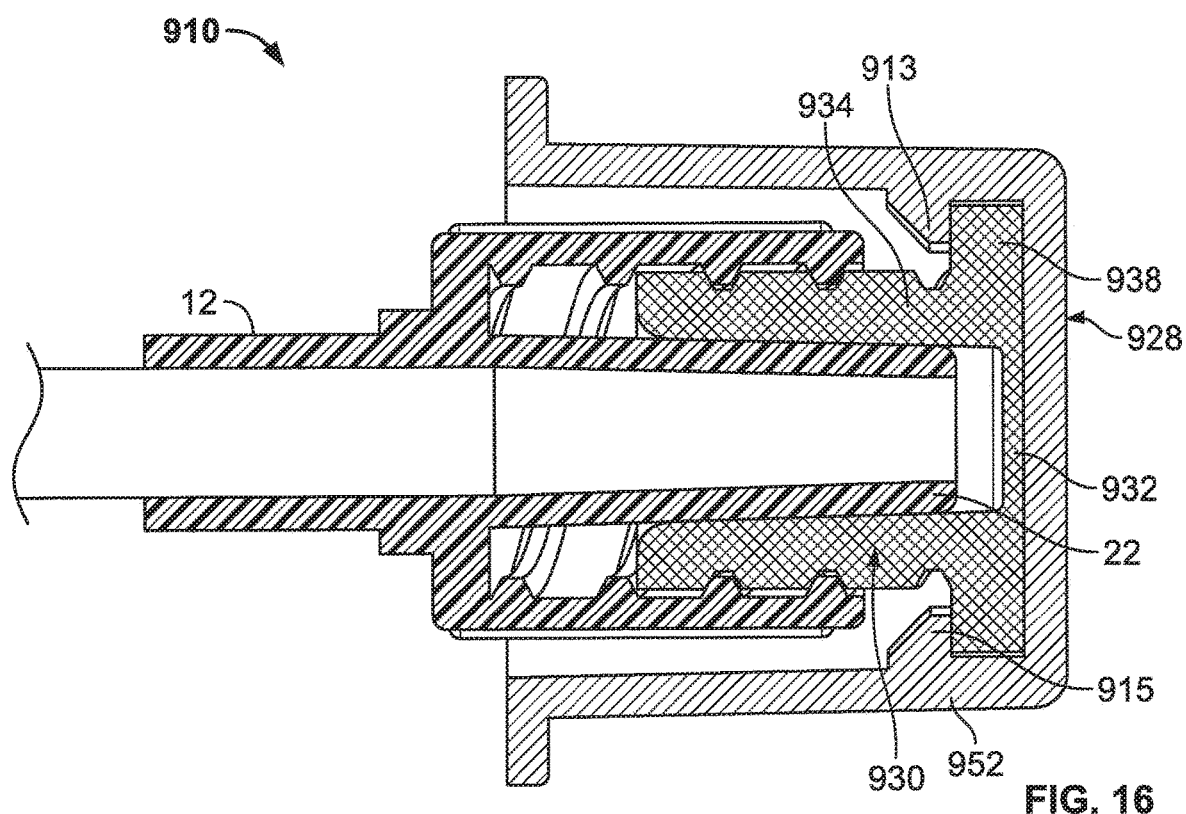
FIG. 16 is a cross-sectional view showing an antiseptic cap assembly that includes a ratchet assembly.
Figure 17:
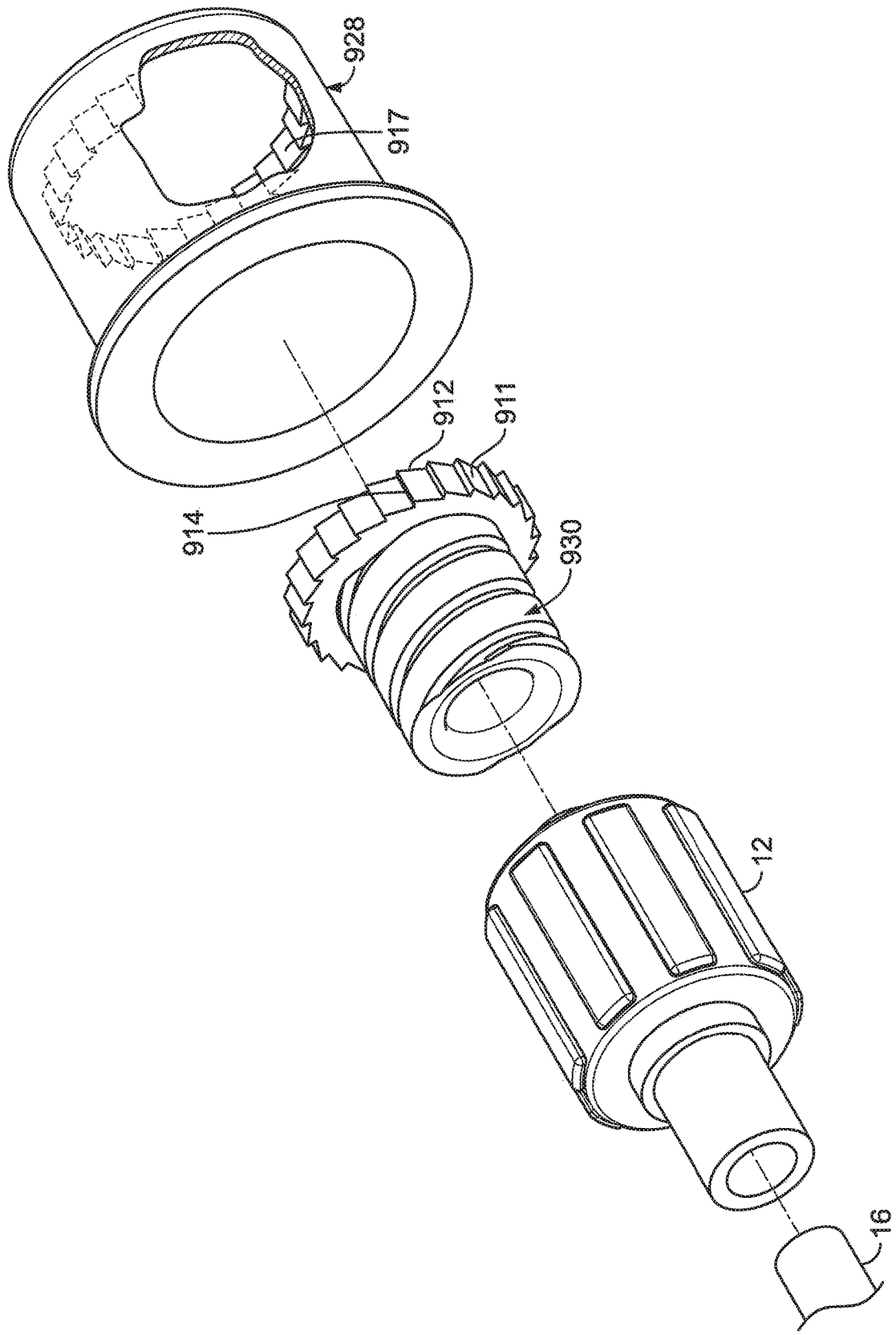
FIG. 17 is an exploded view of the antiseptic cap assembly shown in FIG. 16 and a luer connector.
Figure 18:
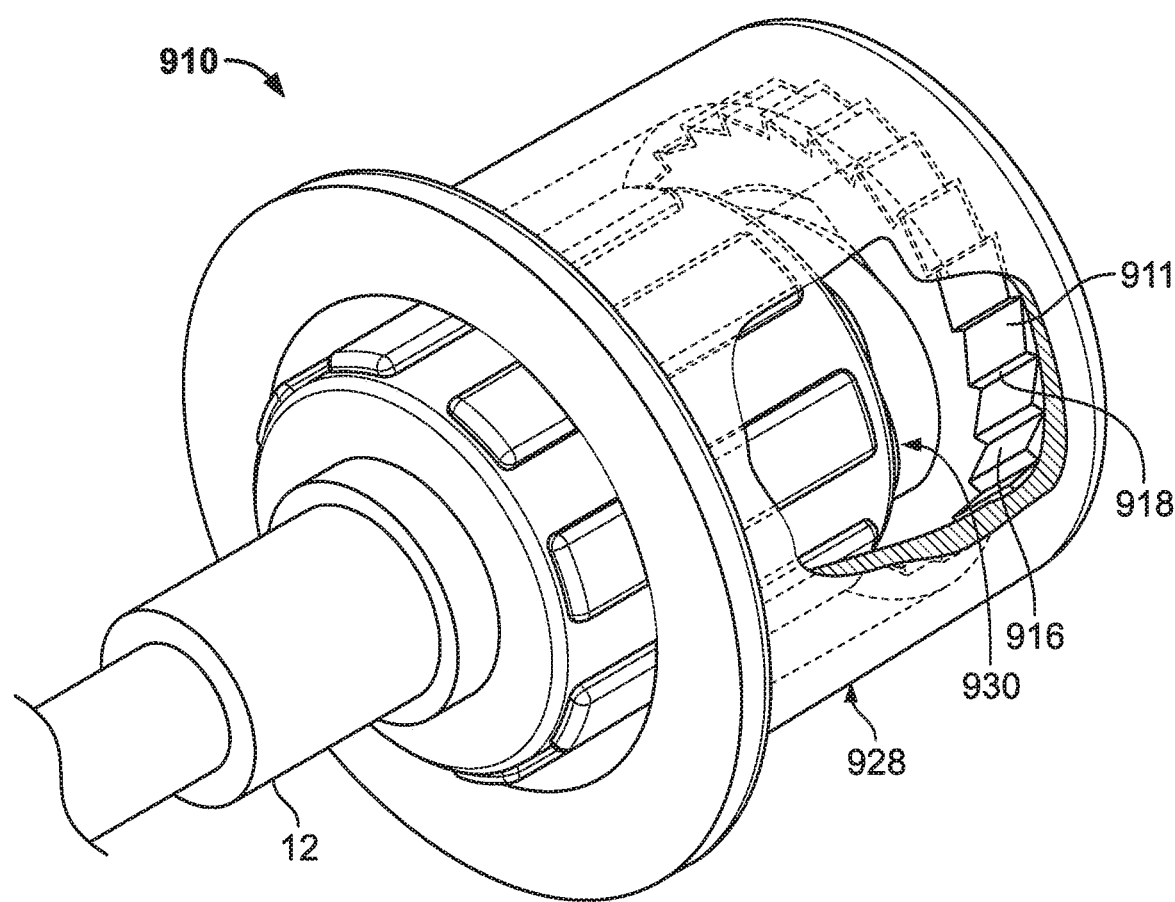
FIG. 18 is a partially cut away perspective view of the antiseptic cap assembly shown in FIG. 16 showing the ratchet assembly.

FIGS. 16-18 show an antiseptic cap assembly, indicated generally as 910, that is sized to engage and disinfect a male luer 22. The antiseptic cap assembly 910 operates and is constructed in manners consistent with the antiseptic cap assembly 10 shown in FIGS. 1-4, unless stated otherwise. Like the antiseptic cap assembly 10, the antiseptic cap assembly 910 includes a cap holder 928 and a cap 930 inserted within the cap holder 928. This embodiment includes a mechanism to prevent overtightening of the cap 930 on the male luer 22 which could damage the male luer 22. This is addressed with a ratchet assembly.

The cap 930 includes a base 932 and an annular threaded portion 934 extending from the base 932. The base 932 includes an outer flange 938 with a plurality of teeth 911 (see FIGS. 17 and 18), along the outer perimeter that allows for rotation in only one direction. Alternatively, it could be configured to allow for rotation in both directions by angling both surfaces of the teeth. The teeth 911 have angled faces 912 and generally perpendicular faces 914.

The cap holder 928 includes a retaining mechanism for retaining the cap 930 in the cap holder 928. The retaining mechanism could include a first protrusion 913 that extends from one section of the sidewall 952 of the cap holder 928, and a second protrusion 915 that extends from an opposite section of the sidewall 952 of the cap holder 928. The first and second protrusions 913, 915 are configured to extend over the base 932 of the cap 930. Alternatively, the retaining mechanism could include a single ring around the interior of the cap holder 928.

The cap holder 928 includes a plurality of teeth 917 that mate with the teeth 911 to form a ratchet mechanism. The teeth 917 interact with the teeth 911 to allow the cap 930 to rotate in the cap holder 928 in only one direction, and have angled faces 916 and generally perpendicular faces 918, like the teeth 911 of the base 932. Alternatively, it could be configured to allow for rotation in both directions.

The ratchet mechanism provides an audible or a tactile feedback to indicate that the antiseptic cap assembly 910 is properly secured. Also, the ratchet mechanism could limit torque to prevent damage to the luer connector 12 or to the cap 930. The cap 930 is threaded on the male luer 22 in accordance with other embodiments of the cap 930. If the cap 930 is turned beyond the limit of the threads, instead of damaging the male luer 22, the cap 930 will slide with respect to the cap holder 928, the angled teeth 911, 917 of the base 932 of the cap 930 and the cap holder 930 respectively sliding past one another to prevent further tightening of the cap 930 onto the male luer 22. When removing the cap 930 from the male luer 22, the generally perpendicular faces 914, 918 engage and do not permit sliding.

Figure 19:
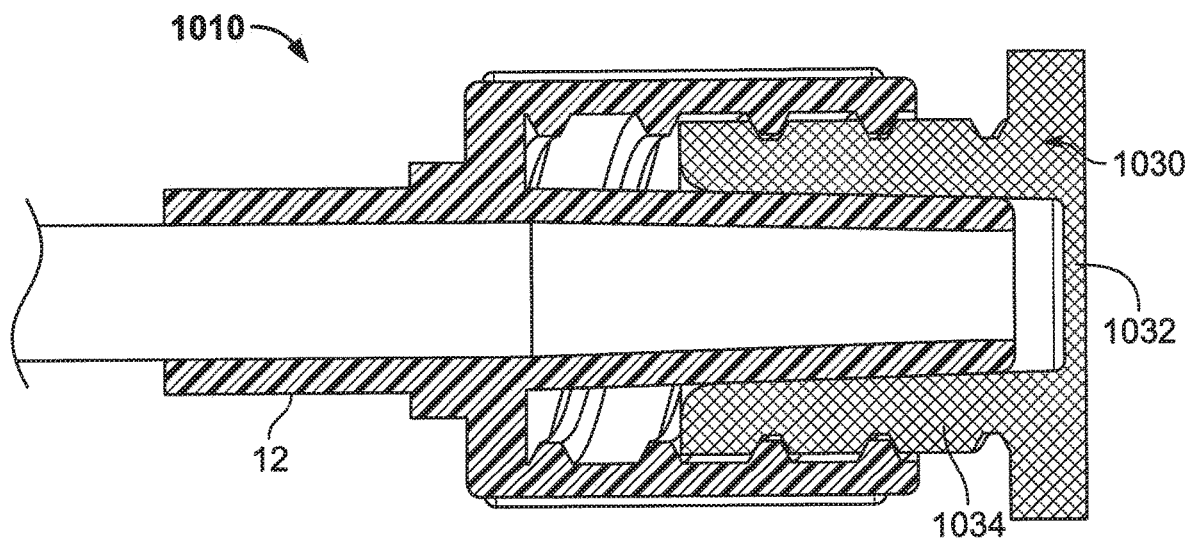
FIG. 19 is a perspective view showing an antiseptic cap assembly without a cap holder.

FIG. 19 shows an antiseptic cap assembly, indicated generally as 1010, that is sized to engage and disinfect a male luer 22. The antiseptic cap assembly 1010 operates and is constructed in manners consistent with the antiseptic cap assembly 10 shown in FIGS. 1-4, unless stated otherwise.

The cap 1030 is used without a cap holder. The cap 1030 includes a base 1032 and an annular threaded portion 1034 extending from the base 1032. Antiseptic fluid can be associated with the interior surface of the annular threaded portion 1034.

The configuration of the cap 1030 is only exemplary. For example, the cap 1030 could be configured without threads and sized to engage the luer connector 12 with a push-on friction fit. Likewise, the cap 1030 could also include a sidewall, like that shown in FIG. 5.

Figure 20:
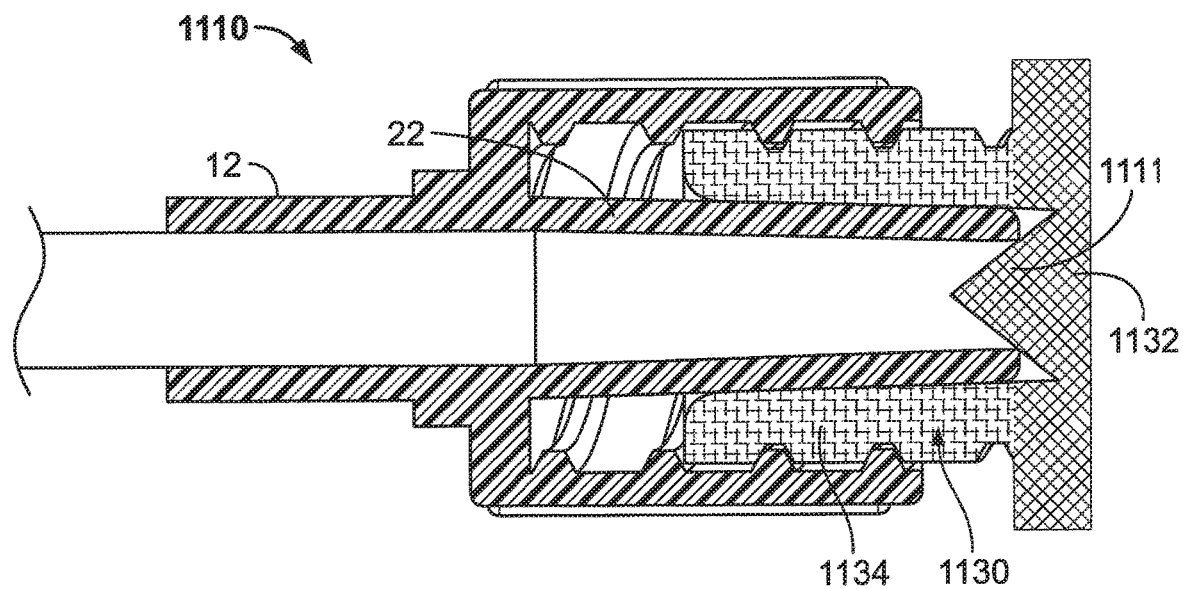
FIG. 20 is a cross-sectional view showing the antiseptic cap assembly of FIG. 19 having hydrophobic and hydrophilic sections.

FIG. 20 shows an antiseptic cap assembly, indicated generally as 1110, that is sized to engage and disinfect a male luer. The antiseptic cap assembly 1110 operates and is constructed in manners consistent with the antiseptic cap assembly 1010 shown in FIG. 18, unless stated otherwise.

At least a portion of the cap 1130 could be treated with a hydrophilic surfactant, or otherwise made hydrophilic. The threaded portion 1134 could be treated with a hydrophilic surfactant whereas the base 1132 could remain hydrophobic, so as to be resistant to and non-absorbent of an antiseptic fluid.

A center plug 1111 could bear against the opening 24 formed in the male luer 22 to prevent the antiseptic fluid from entering the male luer 22. The center plug 1111 could be made of porous plastic and left in a hydrophobic state, thereby inhibiting or minimizing antiseptic fluid from passing therethrough and into the opening 24 formed in the male luer 22. The hydrophobic section could also act as a plug in the IV line to prevent ingress of antiseptic fluid or to stop leakage of IV fluid.

Figure 21:
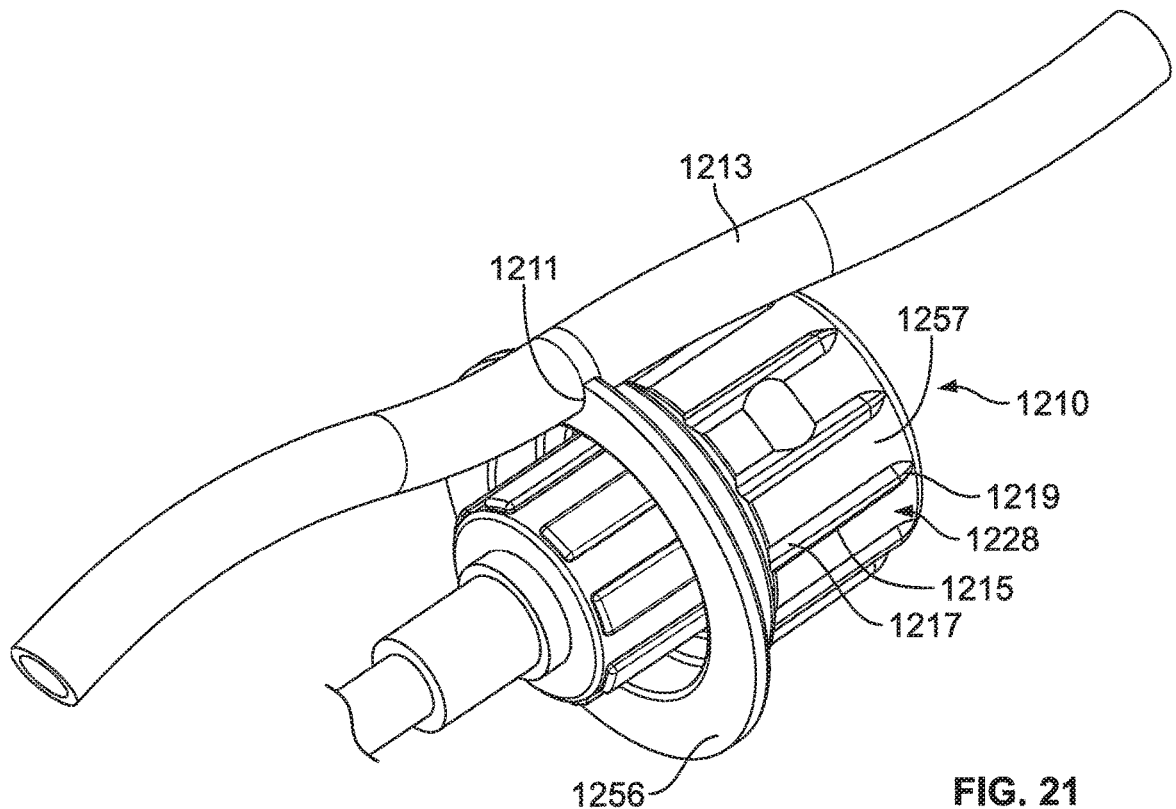
FIG. 21 is a perspective view showing an antiseptic cap assembly, wherein a cap holder has a flange with a recess for receiving a line.

FIG. 21 shows an antiseptic cap assembly, indicated generally as 1210, that is sized to engage and disinfect a male luer 22. The antiseptic cap assembly 1210 operates and is constructed in manners consistent with the antiseptic cap assembly 10 shown in FIGS. 1-4, unless stated otherwise.

The cap holder 1228 has a notch 1211 in an outer flange 1256 that is configured to attached to a supporting surface, such as a fluid line 1213. As shown, the cap holder 1228 has a plurality of ribs 1215 extending along a sidewall 1252 from one end 1217 of the cap holder 1228 to the opposite end 1219 of the cap holder 1228. The ribs 1215 facilitate gripping of the cap holder 1228.

Figure 22:
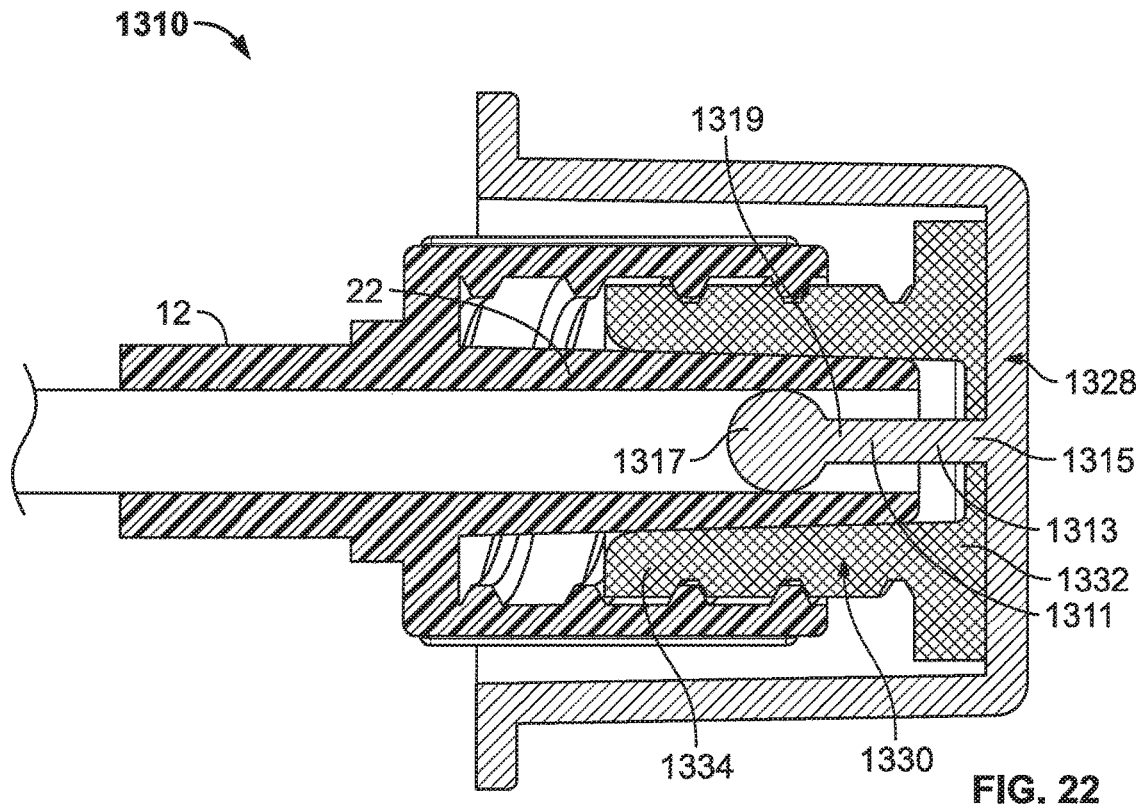
FIG. 22 is a cross-sectional view showing an antiseptic cap assembly, wherein a plug is supported by an arm.

FIG. 22 shows an antiseptic cap assembly, indicated generally as 1310, that is sized to engage and disinfect a male luer. The antiseptic cap assembly 1310 operates and is constructed in manners consistent with the antiseptic cap assembly 10 shown in FIGS. 1-3, unless stated otherwise. Like the antiseptic cap assembly 10, the antiseptic cap assembly 1310 includes a cap holder 1328 and a cap 1330 sized to be positioned within the cap holder 1328.

A sealing mechanism, such as a center plug 1311, is sized to extend from the cap holder 1328 through the base 1332 and is sized to be positioned within the threaded portion 1334 of the cap 1330. As such, the center plug 1311 is made of a non-porous material such as SANTOPRENE, or any other suitable material. In particular, the center plug 1311 includes an arm 1313 with one end 1315 extending from the base 1332, and a sphere 1317 attached to an opposite end 1319 of the arm 1313. The sphere 1317 is configured to bear against the opening 24 formed in the male luer 22 to limit the distance that the antiseptic fluid can travel into the male luer 22. Alternatively, the center plug 1311 could extend from the base 1332 and be made of another material such as rubber. The sphere 1317 could be replaced with a non-spherical device.

Figure 23:
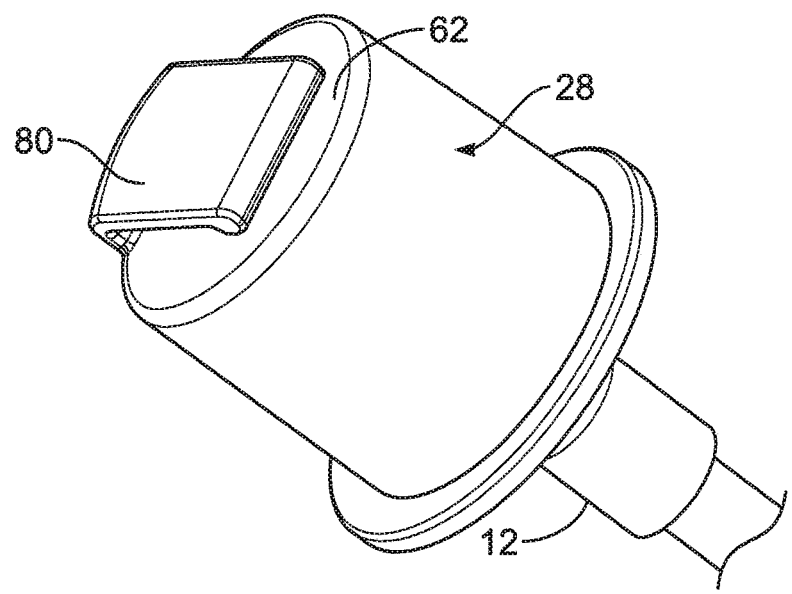
Figure 24:
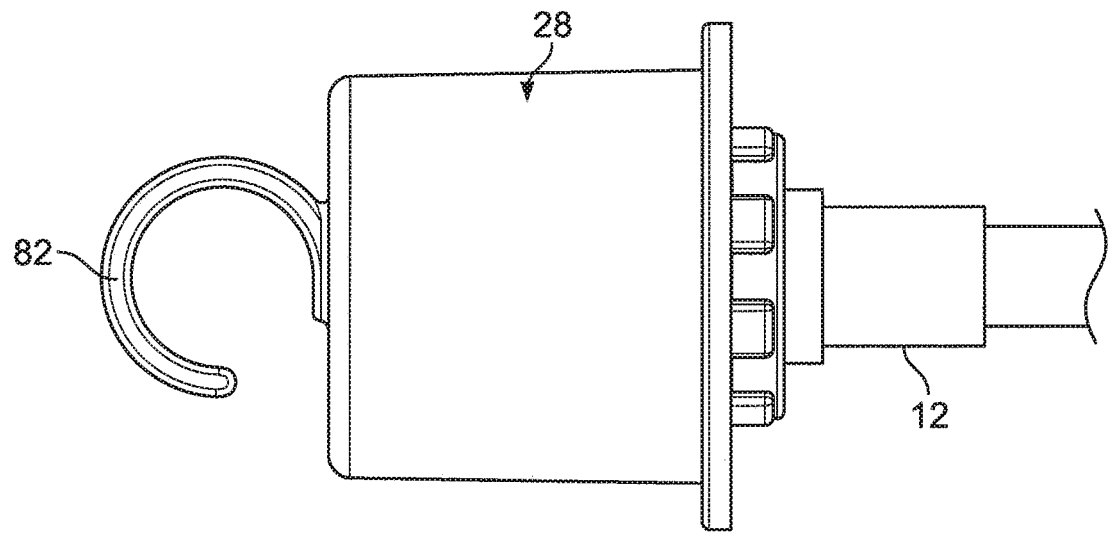

Any of the antiseptic cap assemblies 10, 110, 210, 310, 410, 510, 610, 710, 810, 910, 1010, 1110, 1210, and 1310 disclosed herein could be configured to be removably attached to a suitable surface (not shown), such as a IV bag, IV pump, or IV pole, etc., for use. For example, in FIG. 23, the substantially flat surface 62 of the cap holder 28 includes a clip 80 sized to removeably secure the antiseptic cap assembly 10 to a supporting surface (not shown), such as a IV bag. In FIG. 24, a hook 82 could be provided extending from the substantially flat surface 62 of the cap holder 28 and sized to removeably secure the antiseptic cap assembly 10 to a supporting surface (not shown).

In FIG. 25, a horseshoe-shaped clip 84 could be provided extending from the substantially flat surface 62 of the cap holder 28 and sized to releasably fasten an antiseptic cap assembly 10 to a supporting surface (not shown). The location of a fastening member could vary. For example, in FIG. 26, the sidewall 52 of the cap holder 28 includes a clip 86.

In FIG. 27, the end surface 62 of the cap holder 28 includes an adhesive 88 that could be covered by a release sheet 89. The adhesive 88 could be used to attach the antiseptic cap assembly 10 to a supporting surface, such as a IV pole. A pull tab 90 could be provided to remove the release sheet 89 to expose the adhesive 88.

Alternative fastening mechanisms could be provided. For example, the antiseptic cap assembly could include a ring (not shown).

The antiseptic cap assembly could be incorporated in kits with flush syringes, caps for treating a catheter or needleless connector, and line access devices, etc. The antiseptic fluid used could include an anticoagulant material, and/or an antimicrobial material. Examples of antiseptic fluid that could be used are disclosed in U.S. patent application Ser. No. 11/821,190, filed on Jun. 22, 2007, and Ser. No. 12/214,526, filed on Jun. 19, 2008. The entire disclosures of U.S. patent application Ser. Nos. 11/821,190 and 12/214,526 are incorporated herein by reference in their entirety.

Figure 28:
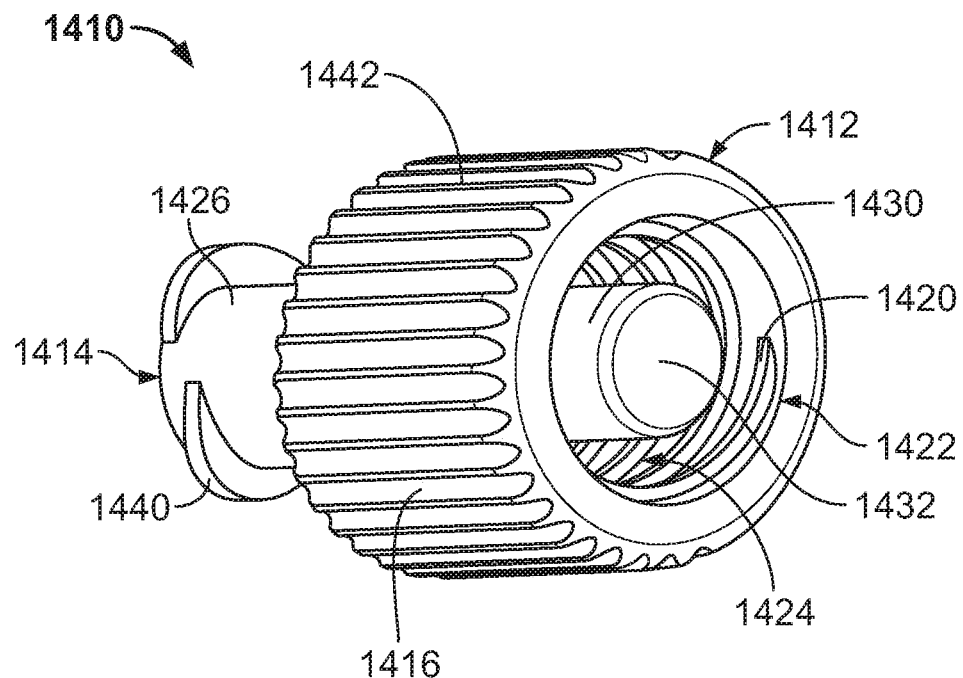
FIG. 28 is a perspective view of an antiseptic dead-end cap.
Figure 29:
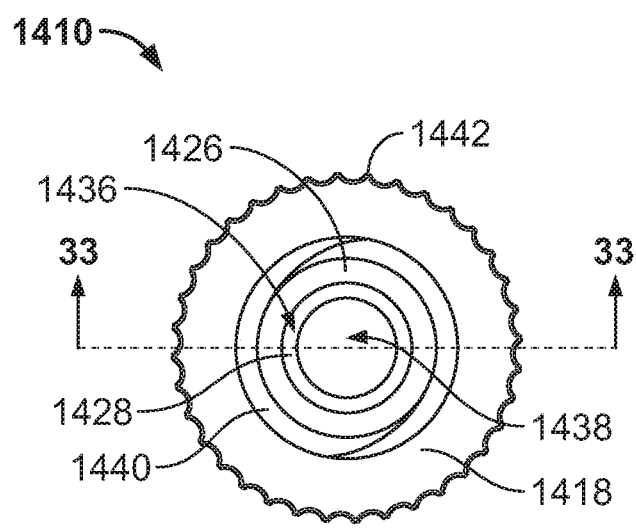
FIG. 29 is a front view of the antiseptic dead-end cap.
Figure 30:
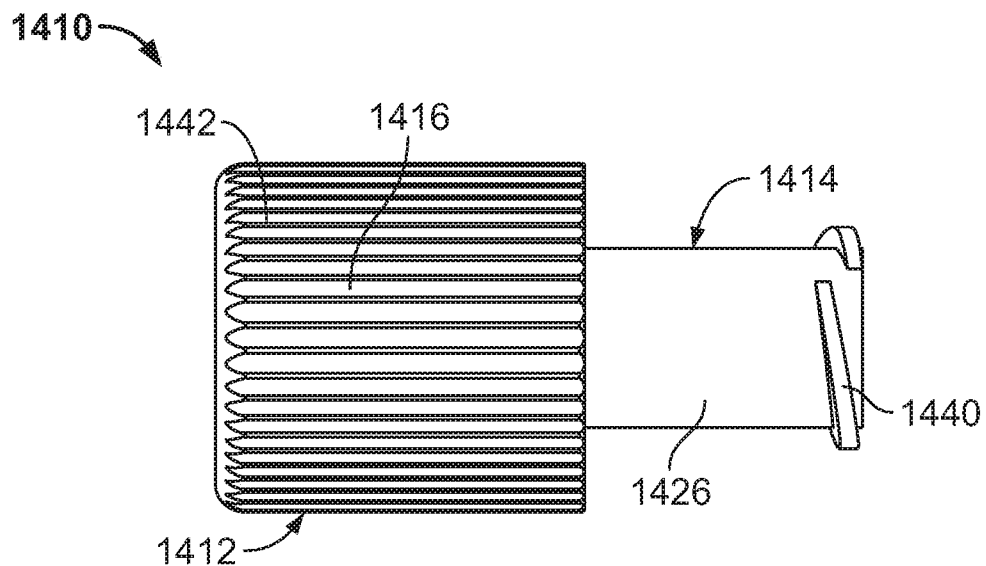
FIG. 30 is a side view of the antiseptic dead-end cap.
Figure 31:
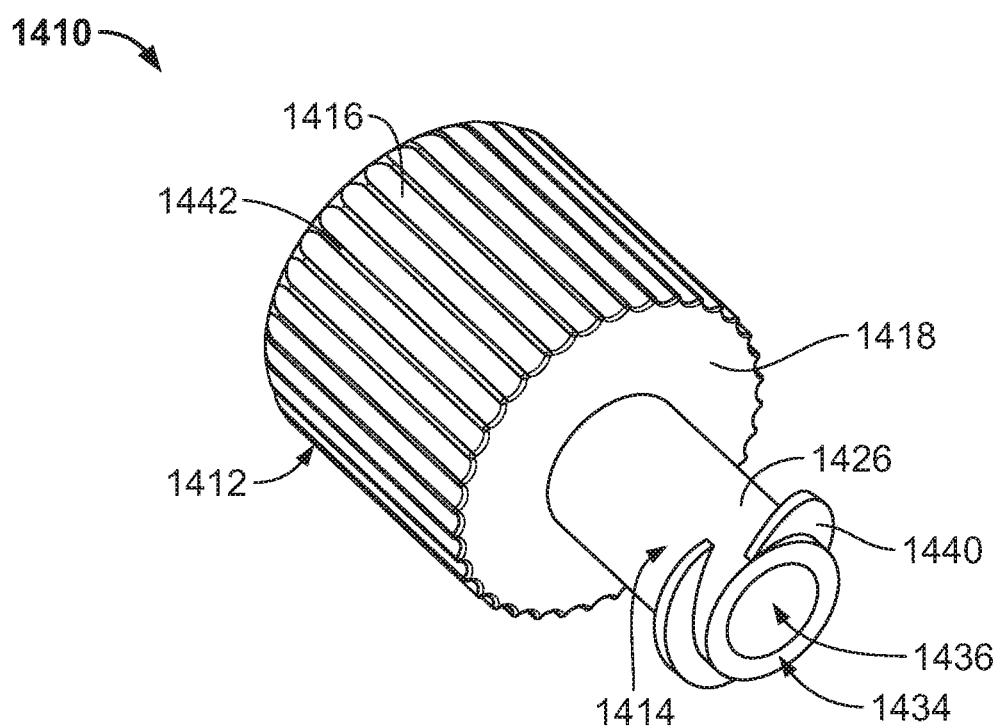
FIG. 31 is another perspective view of the antiseptic dead-end cap.
Figure 32:
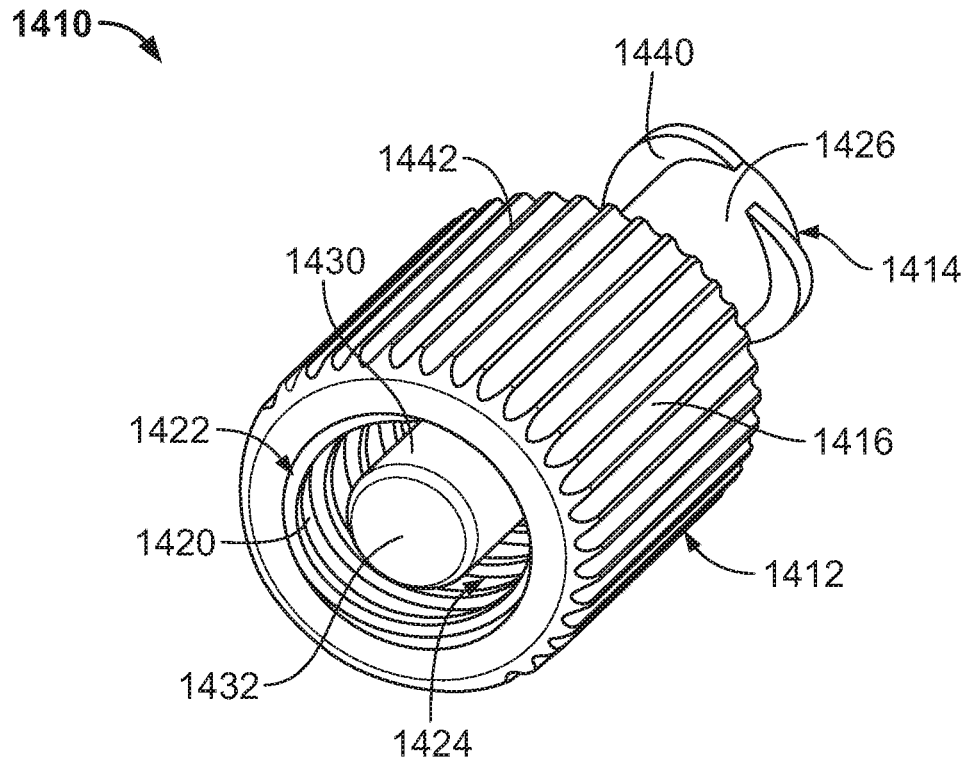
FIG. 32 is another perspective view of the antiseptic dead-end cap.

FIG. 28 is a perspective view of a multifunction antiseptic dead-end cap 1410. The antiseptic dead-end cap 1410 includes a first portion 1412, e.g., a male connector portion, that connects to a female luer (not shown) and a second portion 1414, e.g., a female connector portion, that connects to a male luer (not shown). The male luer or the female luer may, respectively, be attached to a fluid source (not shown), such as an IV bag filled with fluid. For example, the male luer may be the male luer 22 illustrated in FIGS. 1 and 3-27 and described with respect thereto.

As shown in FIGS. 28-33, the first portion 1412 includes a first annular wall 1416 extending from a base 1418. The first annular wall 1416 includes one or more threads 1420 positioned on an interior wall of the first annular wall 1416. The threads 1420 of the first portion 1412 are configured to engage and cooperate with threads of a female luer to allow the dead-end cap 1410 to be securely threadedly connected to the female luer.

The first annular wall 1416 defines an open end 1422. The base 1418 closes the opposite end of the first annular wall 1416. A cylindrical center plug 1430 extends from the base 1418 in the direction of the first annular wall 1416 and is closed by an end wall 1432. The first annular wall 1416 and the cylindrical center plug 1430 are coaxial with one another and the cylindrical center plug 1430 is smaller in diameter than the first annular wall 1416. The first annular wall 1416, the base 1418, and the cylindrical center plug 1430 define a first chamber 1424 that is annular, accessible by the open end 1422, and sized to receive the female luer. When a female luer is inserted through the open end 1422 of the first portion 1412, the cylindrical center plug 1430 and the end wall 1432 are inserted into a portion of the female luer.

The second portion 1414 includes a second annular wall 1426 extending from the base 1418 opposite the direction of the first annular wall 1416, and forms an internal shoulder 1428 with the base 1418. The second annular wall 1426 has an open end 1434 and forms a second chamber 1436, while the cylindrical center plug 1430 and the end wall 1432 form a third chamber 1438. The second chamber 1436 and the third chamber 1438 are in fluidic communication, and the second chamber 1436 is accessible by the open end 1434. The second chamber 1436 is sized to receive a male luer.

One or more threads 1440 are positioned on an exterior wall of the second annular wall 1426. The threads 1440 are configured to engage and cooperate with threads of a male luer connector, such as luer connector 12 shown in FIG. 1. The threads 1440 and the threads of the male luer connector cooperate with each other so as to allow the dead-end cap 1410 to be securely threadedly connected to the male luer connector. The dead-end cap 1410 may include a plurality of external ridges 1442 provided on the first portion 1412 to facilitate gripping of the dead-end cap 1410 during handling and connecting with a connector.

Using the male luer connector 12 shown in FIG. 1 as an example, when the male luer connector 12 engages the second portion 1414, the male luer 22 of the male luer connector 12 is inserted into the open end 1434 and into the second chamber 1436. As the threads 20 of the male luer connector 12 engage the threads 1440 of the second portion 1414, the male luer 22 traverses further into the second chamber 1436 and may traverse into the third chamber 1428. The second annular wall 1426 could be formed with a tapered shape that compliments the male luer 22 of the luer connector 12. In such a configuration, the second annular wall 1426 may narrow from the open end 1434 to the base 1418.

As mentioned above, the antiseptic dead-end cap 1410 has a dual operability wherein it is configured to not only attach to a male luer connector, but also a female luer connector. Generally, a female luer connector can include a circumferential wall that defines a chamber and has external threads. When attaching the dead-end cap 1410 to a female luer connector, the circumferential wall of the female luer connector is inserted through the open end 1422 and into the first chamber 1424, such that the cylindrical center plug 1420 is inserted into the circumferential wall of the female luer connector. The dead-end cap 1410 can be twisted so that the one or more threads 1420 engage the female luer connector, securing the dead-end cap 1410 with the female luer connector.

Figure 33:
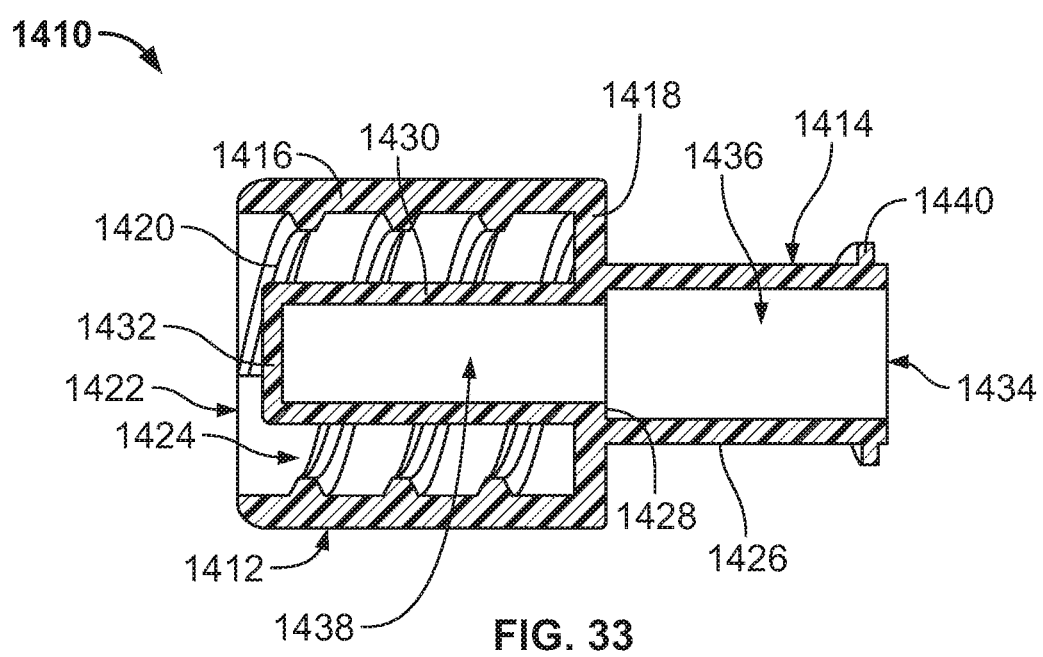
FIG. 33 is a cross-sectional view of the antiseptic dead-end cap of FIG. 28 taken along line 33-33.

FIG. 33 is a cross-section of the multifunction antiseptic dead-end cap 1410 of FIG. 28 taken along line 33-33. FIG.

33 shows the configuration of the dead-end cap 1410 in greater detail. It should be noted that this configuration is exemplary. For example, the dead-end cap 1410 could be configured without the first portion threads 1420 and/or the second portion threads 1440. In such a configuration, the first annular wall 1416 and the cylindrical center plug 1430 may be sized to engage a female luer connector with a push-on friction fit. Similarly, the second annular wall 1426 may be sized to engage a male luer connector with a push-on friction fit.

The dead-end cap 1410 functions to cap a male luer connector and/or a female luer connector so that fluid does not leak from a fluid source. The dead-end cap 1410 may be used for a temporary disconnect of male and female luers so that they do not warrant disposal.

While the antiseptic cap disclosed herein includes male and female connector portions, it could also be provided having just a male or just a female portion. In an arrangement where the antiseptic dead-end cap 1420 includes only a male connector portion, the dead-end cap 1420 could include the base 1418, the first annular wall 1416 extending from the base 1418, the cylindrical center plug 1430 extending from the base 1418 in the direction of the first annular wall 1416 and closed by the end wall 1432, and the plurality of threads 1420. The second annular wall 1426, and the female side of the cap can be eliminated. In an arrangement where the antiseptic dead-end cap 1420 includes only a female connector portion, the dead-end cap 1420 could include the base 1418, the second annular wall 1426 and the threads 1440, with the base 1418 and the second annular wall 1426 defining the second chamber 1436. The first annular wall 1416, and the cylindrical center plug 1430 could be eliminated.

Portions of the antiseptic dead-end cap 1410, such as an inner surface of the first annular wall 1416, the plurality of threads 1420, an outer surface of the second annular wall 1426, an inner surface of the second annular wall 1426, and the second portion threads 1440, could be coated or impregnated with an antiseptic fluid, an anticoagulant fluid, and/or an antimicrobial fluid. An example of a suitable antiseptic fluid is isopropyl alcohol. The concentration of the isopropyl alcohol could vary, and is preferably 70%. The concentration of alcohol could be in a range from 20% to 100%. It will be understand that other materials could be used, such as other alcohols, including ethanol, propanol, and/or butanol, or iodine, hydrogen peroxide, chlorhexidine gluconate, chlorhexidine acetate, etc. The antiseptic, anticoagulant, and/or antimicrobial agent could be in liquid or solid form.

The antiseptic dead-end cap 1410 may be constructed of a material having a 40-60 durometer hardness value on a Shore A scale. The material may be a medium soft to medium hard rubber that is pliable and malleable for purposes of engagement with a luer.

Antiseptic Coatings

It is contemplated that the devices described herein can be coated with an antiseptic coating by any suitable technique such as immersion of the part into an antiseptic solution, by spray coating the part with the antiseptic solution, by blending the antiseptic solution or material into the polymeric material used to fabricate the device.

A quantity of physiological, antimicrobial metal compound is added to the resin for direct molding of an article. Physiological, antimicrobial metals are meant to include the precious metals, such as silver, gold and platinum, and copper and zinc. Physiological, antimicrobial metal compounds used herein include oxides and salts of preferably silver and also gold, for example: silver acetate, silver benzoate, silver carbonate, silver citrate, silver chloride, silver iodide, silver nitrate, silver oxide, silver sulfadiazine, silver sulfate, gold chloride and gold oxide. Platinum compounds such as chloroplatinic acid or its salts (e.g., sodium and calcium chloroplatinate) may also be used. Also, compounds of copper and zinc may be used, for example: oxides and salts of copper and zinc such as those indicated above for silver. Single physiological, antimicrobial metal compounds or combinations of physiological, antimicrobial metal compounds may be used.

Preferred physiological, antimicrobial metal compounds used in this invention are silver acetate, silver oxide, silver sulfate, gold chloride and a combination of silver oxide and gold chloride. The particles of the silver compounds are sufficiently able to be extracted to form a zone of inhibition to prevent and kill bacteria growth.

In another preferred form of the invention the devices herein are impregnated with triclosan and silver compounds or triclosan and chlorhexidine, or chlorhexidine gluconate, or chlorhexidine acetate.

It will be understood that the embodiments described herein are merely exemplary and that a person skilled in the art may make many variations and modifications without departing from the spirit and scope of the invention. All such variations and modifications are intended to be included within the scope of the invention as defined by the appended claims.

What is claimed is:

1. An antiseptic cap comprising:
 a rigid housing comprising a housing bottom wall and a housing sidewall extending from the housing bottom wall at least partially surrounding an interior chamber and an opening into the interior chamber;
 a non-threaded interior surface portion extending at least partially along the housing sidewall from the opening and towards the bottom wall, the non-threaded interior surface portion being compressible and being configured to directly engage and securely attach the antiseptic cap to a medical device;
 an antiseptic liquid being positioned within the rigid housing; and
 a seal being removably attached to an outer surface of the rigid housing and extending over the interior chamber such that the antiseptic liquid is exposed upon removal of the seal.

2. The antiseptic cap of claim 1, wherein the interior surface portion is separate from the rigid housing.

3. The antiseptic cap of claim 1, wherein the interior surface portion is configured to attach to a threaded portion of the medical device.

4. The antiseptic cap of claim 1, wherein the interior surface portion is configured to expand and receive the medical device when the antiseptic cap is securely attached to the medical device.

5. The antiseptic cap of claim 1, wherein the interior surface portion is configured to securely attach to the medical device as the antiseptic cap is applied to the medical device in a direction along a longitudinal axis of the antiseptic cap.

6. The antiseptic cap of claim 1, wherein the rigid housing further comprises a plurality of ribs configured to facilitate attachment of the antiseptic cap to the medical device, and wherein each of the plurality of ribs extend at least partially along an external surface of the housing sidewall.

7. The antiseptic cap of claim 1, wherein the interior surface portion is configured to securely attach to the medical device, wherein the interior surface portion is separate from the rigid housing, wherein the interior surface portion is configured to expand and receive a threaded portion of the medical device when the antiseptic cap is securely attached to the medical device, and wherein the rigid housing further comprises a plurality of ribs configured to facilitate attachment of the antiseptic cap to the medical device, and wherein each of the plurality of ribs extend at least partially along an external surface of the housing sidewall.

8. A combination of the antiseptic cap of claim 1 and the medical device.

* * * * *